(12) United States Patent
Collins et al.

(10) Patent No.: US 9,921,210 B2
(45) Date of Patent: Mar. 20, 2018

(54) HIGH MANNOSE GLYCANS

(75) Inventors: Brian Edward Collins, Arlington, MA (US); Jay Duffner, Shirley, MA (US); Carlos J. Bosques, Arlington, MA (US); Dorota A. Bulik, Malden, MA (US); James Myette, Waltham, MA (US); James Meador, Framingham, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/637,974

(22) PCT Filed: Apr. 7, 2011

(86) PCT No.: PCT/US2011/031637
§ 371 (c)(1),
(2), (4) Date: Mar. 8, 2013

(87) PCT Pub. No.: WO2011/127322
PCT Pub. Date: Oct. 13, 2011

(65) Prior Publication Data
US 2013/0231255 A1    Sep. 5, 2013

Related U.S. Application Data

(60) Provisional application No. 61/321,857, filed on Apr. 7, 2010.

(51) Int. Cl.
*G01N 33/50* (2006.01)
*C12P 21/00* (2006.01)
*G01N 33/68* (2006.01)
*C12Q 1/34* (2006.01)
*H01J 49/00* (2006.01)

(52) U.S. Cl.
CPC ........ *G01N 33/5005* (2013.01); *C12P 21/005* (2013.01); *C12Q 1/34* (2013.01); *C12Y 302/01096* (2013.01); *C12Y 302/01113* (2013.01); *G01N 33/6803* (2013.01); *G01N 33/6854* (2013.01); *C07K 2319/30* (2013.01); *G01N 2333/924* (2013.01); *G01N 2440/38* (2013.01); *H01J 49/00* (2013.01)

(58) Field of Classification Search
None
See application file for complete search history.

(56) References Cited

U.S. PATENT DOCUMENTS

| | | |
|---|---|---|
| 4,859,449 A | 8/1989 | Mattes |
| 5,047,335 A | 9/1991 | Paulson et al. |
| 5,068,190 A | 11/1991 | Horiuchi et al. |
| 5,234,905 A | 8/1993 | Kolhouse et al. |
| 5,340,453 A | 8/1994 | Jackson |
| 5,360,817 A | 11/1994 | von Izstein et al. |
| 5,370,872 A | 12/1994 | Cryz et al. |
| 5,411,942 A | 5/1995 | Widmer et al. |
| 5,456,909 A | 10/1995 | Marsh, Jr. et al. |
| 5,459,031 A | 10/1995 | Blumen et al. |
| 5,500,342 A | 3/1996 | Miyamura et al. |
| 5,510,261 A | 4/1996 | Goochee et al. |
| 5,554,730 A | 9/1996 | Woiszwillo et al. |
| 5,559,103 A | 9/1996 | Gaeta et al. |
| 5,567,684 A | 10/1996 | Ladisch et al. |
| 5,663,355 A | 9/1997 | Ganem et al. |
| 5,667,984 A | 9/1997 | Parekh et al. |
| 5,679,321 A | 10/1997 | Dasgupta et al. |
| 5,712,254 A | 1/1998 | Chaki et al. |
| 5,723,583 A | 3/1998 | Seed et al. |
| 5,753,454 A | 5/1998 | Lee |
| 5,759,823 A | 6/1998 | Wong et al. |
| 5,856,143 A | 1/1999 | Nilsson |
| 5,879,912 A | 3/1999 | Roth |
| 5,945,322 A | 8/1999 | Gotschlich |
| 6,030,815 A | 2/2000 | DeFrees et al. |
| 6,048,707 A | 4/2000 | Klock, Jr. |
| 6,096,555 A | 8/2000 | Hermentin et al. |
| 6,132,994 A | 10/2000 | Tawada et al. |
| 6,156,547 A | 12/2000 | Roth |
| 6,159,954 A | 12/2000 | Maruyama et al. |
| 6,190,522 B1 | 2/2001 | Haro |
| 6,218,149 B1 | 4/2001 | Morrison et al. |
| 6,261,805 B1 | 7/2001 | Wood |
| 6,274,568 B1 | 8/2001 | Schnaar et al. |
| 6,280,989 B1 | 8/2001 | Kapitonov et al. |
| 6,284,516 B1 | 9/2001 | Pollock et al. |
| 6,358,710 B1 | 3/2002 | Graves et al. |
| 6,597,996 B1 | 7/2003 | Venkataraman et al. |
| 8,034,906 B2 | 10/2011 | Borhani et al. |
| 9,170,249 B2 | 10/2015 | Washburn et al. |

(Continued)

FOREIGN PATENT DOCUMENTS

| | | |
|---|---|---|
| CN | 101001875 A | 7/2007 |
| CN | 101137757 A | 3/2008 |
| JP | 2005509403 A | 4/2005 |
| WO | 2000/065070 A2 | 11/2000 |
| WO | 200180884 A1 | 11/2001 |
| WO | 200200879 A2 | 1/2002 |
| WO | 03/025133 A2 | 3/2003 |
| WO | 2007011041 A1 | 1/2007 |
| WO | 2007087384 A2 | 8/2007 |
| WO | WO200863982 * | 5/2008 |

(Continued)

OTHER PUBLICATIONS

Hoja-Lukowicz et al. Glycobiology vol. 10 No. 6 pp. 55 1-557. 2000.*
Gates et al. Glycoprotein Analysis Manual, 1st ed. Sigma-Aldrich, St. Louis, MO 2004, pp. 1-87 as cited in the IDS dated Oct. 4, 2013.*
Kanda et al. Glycobiology vol. 17 No. 1 pp. 104-118, 2006.*
Millward et al. Biologicals 36 (2008) 41-47.*
Freeze et al. Current protocols in cell biology (1999): 15-2.*

(Continued)

*Primary Examiner* — Paul J Holland
(74) *Attorney, Agent, or Firm* — Brenda Herschbach Jarrell; Rolando Medina; Nishat A. Shaikh

(57) ABSTRACT

Methods and compositions related to high mannose glycans are described.

12 Claims, 6 Drawing Sheets

(56) References Cited

U.S. PATENT DOCUMENTS

| | | | |
|---|---|---|---|
| 2002/0054878 A1 | 5/2002 | Lowman et al. | |
| 2003/0157108 A1 | 8/2003 | Presta | |
| 2003/0211573 A1 | 11/2003 | Ryll | |
| 2004/0077836 A1 | 4/2004 | DeFrees et al. | |
| 2004/0210396 A1 | 10/2004 | Fischer et al. | |
| 2006/0040353 A1 | 2/2006 | Davidson et al. | |
| 2006/0127950 A1* | 6/2006 | Bosques et al. | 435/7.1 |
| 2006/0252672 A1 | 11/2006 | Betenbaugh et al. | |
| 2008/0227136 A1 | 9/2008 | Pla et al. | |
| 2008/0261301 A1 | 10/2008 | Kanda et al. | |
| 2008/0280324 A1 | 11/2008 | Rouwendal et al. | |
| 2009/0041770 A1 | 2/2009 | Chamberlain et al. | |
| 2009/0069232 A1 | 3/2009 | Callewaert et al. | |
| 2009/0104603 A1 | 4/2009 | Satomaa et al. | |
| 2009/0203550 A1 | 8/2009 | Venkataraman et al. | |
| 2009/0226968 A1 | 9/2009 | Betenbaugh et al. | |
| 2009/0258014 A1 | 10/2009 | Laterra et al. | |
| 2009/0311732 A1 | 12/2009 | Rossi et al. | |
| 2009/0317834 A1 | 12/2009 | Laine et al. | |
| 2010/0048456 A1 | 2/2010 | DeFrees et al. | |
| 2010/0081150 A1 | 4/2010 | Liu et al. | |
| 2010/0113294 A1 | 5/2010 | Venkataraman et al. | |
| 2010/0129843 A1 | 5/2010 | Parsons et al. | |
| 2010/0144553 A1 | 6/2010 | Bosques et al. | |
| 2010/0173323 A1* | 7/2010 | Strome et al. | 435/7.1 |
| 2011/0280873 A1 | 11/2011 | Presta et al. | |

FOREIGN PATENT DOCUMENTS

| | | | |
|---|---|---|---|
| WO | WO2008063982 | * | 5/2008 |
| WO | 2008128228 A1 | | 10/2008 |
| WO | 2008128230 A1 | | 10/2008 |
| WO | 2008130926 A2 | | 10/2008 |
| WO | 2010136492 A2 | | 12/2010 |
| WO | 2010138502 A2 | | 12/2010 |
| WO | 2010141855 A1 | | 12/2010 |
| WO | 2011127322 A1 | | 10/2011 |
| WO | 2011127325 A1 | | 10/2011 |

OTHER PUBLICATIONS

Akiyama et al., "Analysis of the role of glycosylation of the human fibronectin receptor", J. Biol. Chem. vol. 264(30) pp. 18011-18018 (1989).

Andersen et al., "Multiple cell culture factors can affect the glycosylation of Asn-184 in CHO-produced tissue-type plasminogen activator", Biotechnol. Bioeng., 2000, vol. 70, pp. 25-31.

Andrade et al., "Solid-phase oligosaccharide synthesis: preparation of comlex structures using a novel linker and different glycosylating agents", Org. Lett., 1999, vol. 1, No. 11, pp. 1811-1814.

Baker et al., "Metabolic control of recombinant protein N-glycan processing in NSO and CHO cells", Biotechnol. Bioeng., 2001, vol. 73, pp. 188-202.

Bonne et al., "Sweet—WWW-based rapid 3D construction of oligo- and polysaccharides", Bioinformatics, Sep. 1999, vol. 15, No. 9, pp. 767-768, XP 001024942 ISSN: 1367-4803, Oxford University Press, Surrey, GB.

Bollati-Foglin et al., "Temperature reduction in cultures of hGM-CSF-expressing CHO cells: effect on productivity and product quality", Biotechnol. Prog., 2005, vol. 21, pp. 17-21.

Bowman et al., "Biosynthesis of L-selectin ligands: sulfation of sialyl Lewis x-related oligosaccharides by a family of GlcNAc-6-sulfotransferases", Biochemistry, 2001, vol. 40, No. 18, pp. 5382-5391.

Breidenbach et al., "Targeted metabolic labeling of yeast N-glycans with unnatural sugars" Proc. Natl. Acad. Sci., vol. 107(9) pp. 3988-3993 (2010).

Broschat et al., "Purification and characterization of GDP-D-mannose 4,6-dehydratase from porcine", Thyroid. Eur. J. Biochem., 1985, vol. 153, No. 2, pp. 397-401.

Cabrera et al., "Influence of culture conditions of the N-glycosylation of a monoclonal antibody specific for recombinant hepatitis B surface antigen", Biotechnol. Appl. Biochem., 2005, vol. 41, pp. 67-76.

Chen et al., "Independent Lec1A CHO Glycosylation Mutants Arise from Point Mutations in N-Acetylglucosaminyltransferase I that Reduce Affinity for Both Substrates. Molecular Consequences Based on the Crystal Structure of GlcNac—TI", Biochemistry vol. 40(30) pp. 8765-8772 (2001).

Chen et al., "T cell receptors signaling co-regulates multiple *Golgi* genes to enhance N-glycan branching" J. Boil. Chem. vol. 284(47) pp. 32454-32461 (2009).

Clark et al., "Gene-expression profiles for five key glycosylation genes for galactose-fed CHO cells expression recombinant IL-4/13 cytokine trap", Biotechnol. and Bioeng., 2005, vol. 90, No. 5, pp. 568-577.

Cooper et al., "GlycoSuiteDB: a curated relational database of glycoprotein glycan structures and their biological sources. 2003 update", Nucleic Acids Research, 2003, vol. 31, No. 1, pp. 511-513.

Cooper et al., "GlycoSuiteDB: a new curated relational database of glycoprotein glycan structures and their biological sources", Nucleic Acids Research, 2001, vol. 29, No. 1, pp. 332-335.

Crowell et al., "Amino acid and manganese supplementation modulates the glycosylation state of erythropoietin in a CHO culture system", Biotechnol. and Bioeng., 2006, pp. 538-549.

Debray et al, "Glycoprotein Analysis: General Methods", In: "Encyclodpedia of Analytical Chemistry" pp. 1-39.

Donaldson et al., "The use of lectins to select subpopulations of insect cells", Biotechnol. and Bioeng., 1999, vol. 61, pp. 616-619.

Drecktrah et al., "Inhibition of a Golgi complex lysophospholipid acyltransferase induces membrane tuble formation and retrograde trafficing" Mol. Biol. Cell, vol. 14(8) pp. 3459-3469 (2003).

European Patent Office, Communication pursuant to Article 96(2) mailed Oct. 30, 2007 in related European Patent Application No. 02 773 390.6.

Extended European Search Report from European Application No. 11766759.2 dated Aug. 19, 2013.

Fareed, "S-9-10 synthetic and biotechnology derived glycomimetics", Impact on Drug Development, 2000, Database Google 6th Annual Pg Forum, Abstract.

Ferrara et al., "Modulation of therapeutic antibody effector functions by glycosylation engineering: influence of golgi enzyme localization domain and co-expression of heterologous b 1, 4-N-acetylglucosaminyltransferase III and golgi a-mannosidase II", Biotechnol. and Bioeng., 2006, vol. 93, No. 5, pp. 851-861.

Fitz et al., "Combined use of subtilisin and N-acetyl neuraminic acid aldolase for the synthesis of a fluorescent sialic acid", J. Org. Chem., 1994, vol. 59, pp. 8279.

Forno et al., "N- and O-linked carbohydrates and glycosylation site occupancy in recombinant human granulocytemacrophage colony-stimulating factor secreted by a Chinese hamster overy cell line", Eur. J. Biochem., 2004, vol. 271, pp. 907-919.

Fukuda et al., "Survival of recombinant erythropoietin in the circulation: the role of carbohydrates", Blood, 1989, vol. 73, pp. 84-89.

Gates et al., "Glycoprotein analysis manual" internet citation, pp. 1-89, retrieved from the Internet:URL:download.bioon.com.cn/view/upload/201301/27194411_2997.pdf.

Gawlitzek et al., "Ammonium alters N-glycan structures of recombinant TNFR-IgG: degradative versus biosynthetic mechanisms", Biotechnol. and Bioeng., 2000, vol. 68, No. 6, pp. 637-646.

Gawlitzek et al., "Characterization of changes in the glycosylation pattern of recombinant proteins from BHK-21 cells due to different culture conditions", Journal of Biotechnology, 1995, vol. 42, pp. 117-131.

Goldman et al., "Monitoring recombinant human interferon-g N-glycosylation and during perfused fluidized-bed and stirred-tank batch culture of CHO cells", Biotechnol. and Bioeng., 1998, vol. 60, pp. 598-607.

Gu et al., "Improvement of interferon-g sialylation in Chinese hamster ovary cell culture by feeding of N-acetylmannosamine", Biotechnol. and Bioeng., 1998, vol. 58, pp. 642-648.

(56) References Cited

OTHER PUBLICATIONS

Harue Imai-Nishiya et al., "Double knockdown of a 1,6 fucosyltransferase (FUT8) and GDP-mannose 4,6-dehydratase (GMD) in antibody-producing cells: a new strategy for generating fully non-fucosylated therapeutic antibodies with enhanced ADCC", BMC Biotechnology, 2007, vol. 7, No. 84, pp. 1-13.
Hewitt et al., "Solution and solid-support synthesis of a potential leishmaniasis carbohydrate vaccine", J. Org. Chem., 2001, vol. 15, No. 66(12), pp. 4233-4243.
Hills et al., "Metabolic control of recombinant monoclonal antibody N-glycosylation in GS-NSO cells", Biotechnol. and Bioeng., 2001, vol. 75, pp. 239-251.
Hirabayashi et al., "Separation technologies for glycomics", J. Chromatog. B Analyst. Biomed. Life Sci., May 2002, 771, No. 1-2, pp. 67-87, Database Medline, US National Library of Medicine, Abstract.
Hoja-Lukowicz et al., "High-mannose-type oligosaccharides form human placental arylsulfatase A are core fucosylated as confirmed bu MALDI MS", Gyclobiology, vol. 10, No. 6, pp. 551-557 (2000).
Hossler et al., "Systems analysis of N-glycan processing in mammalian cells" PLoS One, vol. 2(8)e713 pp. 1-17 (2007).
International Preliminary Report on Patenability including the Written Opinion from International Application Serial No. PCT/US2010/036058 dated Nov. 19, 2010.
International Preliminary Report on Patentability for International Application No. PCT/US2011/031637 dated Oct. 18, 2012.
International Preliminary Report on Patentability from PCT Application Serial No. PCT/US2008/060354 dated Apr. 2, 2009.
International Preliminary Report on Patentability including the Written Opinion for International Application Serial No. PCT/US2011/031641 dated Aug. 17, 2011.
International Search Report and Written Opinion for corresponding International Application Serial No. PCT/US2011/31637 dated Aug. 30, 2011.
International Search Report for PCT/US2002/29285 filing date Dec. 23, 2002.
International Search Report for PCT/US2004/04423, dated Dec. 28, 2004.
International Search Report for PCT/US2010/36058, dated Nov. 19, 2010.
International Search Report for PCT/US2010/37454, dated Sep. 1, 2010.
International Search Report including the Written Opinion for International Application Serial No. PCT/US2011/031641 dated Aug. 17, 2011.
International Search Report including the Written Opinion for International Application Serial No. PCT/US2012/18759 dated Sep. 4, 2012.
International Search Report including Written Opinion for PCT/US2012/28759 dated Sep. 4, 2012.
Kakehi et al., "Analysis of glycoproteins, glycopeptides and glycoprotein-derived polysaccharides by high-performance capillary electrophoresis", J. Chromatogr. A., 1996, vol. 720, No. 1-2, pp. 377-393.
Kanda et al., "Comparison of biological activity among nonfucosylated therapeutic IgF1 antibodies with three different N-linked Fc oligosaccharides: the high-mannose, hybride, and complex types" Glycobiology, vol. 17(1) pp. 104-118 (2007).
Kanda et al., "Establishment of a GDP-mannose 4,6-dehydratase (GMD) knockout host cell line: A new strategy for generating completely non-cucosylated recombinant therapeutics" Journal of Biotechnology, vol. 130 pp. 300-310 (2007).
Kawashima et al., "Tyrosine kinase activity of epidermal growth factor receptor is regulated by GM3 binding through carbohydrate to carbohydrate interactions" J. Biol. Chem. vol. 284(10) pp. 6147-6155 (2009).
Keiser et al., "Direct isolation and sequencing of specific protein-binding glycosaminoglycans", Nature Medicine, 2001, vol. 7, No. 1, pp. 123-128.
Keppler et al., "Biosynthetic modulation of sialic acid-dependent virus-receptor interactions of two primate polyoma viruses", J. Biol. Chem., 1995, vol. 270, No. 3, pp. 1308-1314.
Kim et al., "Production and N-glycan analysis of secreted human erythropoietin glycoprotein in stably transfected *Drosophilia* S2 cells", Biotechnol. and Bioeng., 2005, vol. 92, No. 4, pp. 452-461.
Kosa et al., "Modification of cell surfaces by enzymetic introduction of special sialic acid analogues", Biochm. Biophys. Res. Commun., 1993, vol. 190, pp. 914.
Kunkel et al., "Comparisons of the glycosylation of a monoclonal antibody produced under nominally identical cell culture conditions in two different bioreactors", Biotechnol. Prog., 2000, vol. 16, pp. 462-470.
Kunkel et al., "Dissolved oxygen concentration in serum-free continuous culture affects N-linked glycosylation of a monoclonal antibody", Journal of Biotechnology, 1998, vol. 62, pp. 55-71.
Le Floch et al., "HPCE monitoring of the N-glycosylation pattern and sialylation of murine erythropoietin produced by CHO cells in batch processes", Biotechnol. Prog., 2004, vol. 20, pp. 864-871.
Lin et al., "Unusual stereoselectivity in sialic acid aldolase-catalyzed aldol condensations: synthesis of both enantiomers of high-carbon monosaccharides", J. Am. Chem. Soc., 1992, vol. 114, pp. 10138-10145.
Lipscomb et al., "Effect of production method and gene amplification on the glycosylation pattern of a secreted reported protein in CHO cells", Biotechnol. Prog., 2005, vol. 21, pp. 40-49.
Live et al., "Conformational influences of a glycosylation of a peptide: a possible model for the effect of glycsylation on the rate of protein folding", Proceedings of the National Academy of Sciences of the United States of America, 1996, vol. 93, No. 23, pp. 12759-12761, XP002293395 ISSN: 0027-8424.
Lopez-Avalos et al., "The UDPase activity of the Kluyveromyces lactis Golgi GDPase has a riole in uridine nucleotide sugar transport into Golgi vesicles", Glycobiology, vol. 11(5) pp. 413-422 (2001).
Macmillan et al.,"Selective in vitro glycosylation of recombinant proteins: semi-synthesis of novel homogeneous glycoforms of human erythropoietin", Chemistry and Biology, 2001, vol. 8, pp. 133-145.
Moran et al., "A systematic approach to the validation of process control parameters for monoclonal antibody production in fed-batch culture of a murine myeloma", Biotechnol. and Bioeng., 2000, vol. 69, No. 3, pp. 242-255.
Mueller et al., "Recombinant glycoprotein product quality in proliferation-controlled BHK-21 cells", Biotechnol. and Bioeng., 1999, vol. 65, No. 5, pp. 529-536.
Nairn et al., "Regulation of glycan structures in animal tissues: transcript profiling of glycan-related genes" J. Biol. Chem., vol. 282(25) pp. 17298-17313 (2008).
Nyberg et al ., "Metabolic effects on recombinant interferon-g glycosylation in continuous culture of Chinese hamster ovary cells", Biotechnol. and Bioeng., 1999, vol. 62, No. 3.
Oh et al.,"Effect of N-acetylcystein on butyrate-treated Chinese hamster overy cells to improve the production of recombinant human interferon-b-1a", Biotechnol. Prog., 2005, vol. 21, pp. 1154-1164.
Pace et al., "Characterization of Minor N-linked Glycans on Antibodies Using Endo H Release and MALDI-Mass Spectrometry" Analytical Letters, vol. 42, No. 11, pp. 1711-1724 (2009).
Park et al., "Expression of carbamoyl phosphate synthetase I and ornithine transcarbamoylase genes in Chinese hamster ovary dhfr-cells decreases accumulation of ammonium ion in culture media", Journal of Biotechnology, 2000, vol. 81, pp. 129-140.
Plante et al., "Automated solid-phase synthesis of oligosaccharides", Science, 2001, vol. 291, No. 5508, pp. 1523-1527.
Plante et al., "Formation of b-glucosamine and b-mannose linkages using glycosyl phosphates", Org. Lett., 2000, vol. 2, No. 24, pp. 3841-3843.
Reitman et al., "Mouse Lymphoma Cell Lines Resistant to Pea Letin are defective in Fucose Metabolism", J Biol Chem., vol. 255(20) pp. 9900-9906 (1980).

(56) References Cited

OTHER PUBLICATIONS

Restelli et al., "The effect of dissolved oxygen on the production and the glycosylation profile of recombinant human erythropoietin produced from CHO cells", Biotechnology and Bioengineering, 2006, vol. 94, No. 3, pp. 481-494.
Ripka et al., "Two Chinese Hamster Ovary Glycosylation Mutants Affected in the Converstion of GOP-Mannose to GOP-Fucose" Arch Biochem Biophys vol. 249(2) pp. 533-545 (1986).
Ritzenthaler et al., "Reevaluation of the effets of brefeldin A on plant cells using tobacco Bright Yellow 2 cells expressing Golgi-targeted green fluoresent protein and COPI antisera" Plant Cell, vol. 14(1) pp. 237-261 (2002).
Santell et al., "Aberrant metabolic sialylation of recombinant proteins expressed in Chinese hamster ovary cells in high productivity cultures", Biochemical and Biophysical Research Communications, 1999, vol. 258, pp. 132-137.
Sasaki et al.,"Site-specific glycosylation of human recombinant erythropoietin: analysis of glycopeptides of peptides at each glycosylation site by fast atom bombardment mass spectrometry", Biochemistry, 1988, vol. 27, pp. 8618-8626.
Schuster et al., "Improved effector functions of a therapeutic monoclonal Lewis V-specific antibody by glycoform engineering", Cancer Res., 2005, vol. 65, No. 17, pp. 7934-7941.
Senger et al., "Effect of shear stress on intrinsic CHO culture state and glycosylation of recombinant tissue-type plasminogen activator protein", Biotechnol. Prog., 2003, vol. 19, pp. 1199-1209.
Serrato et al., "Heterogeneous conditions in dissolved oxygen affect N-glycosylation but not productivity of a monoclonal anitbody in hybridoma cultures", Biotechnology and Bioengineering, 2004, vol. 88, No. 2, pp. 176-188.
Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives", Glycobiology, 1991, vol. 1, pp. 187-191.
Sokolowski et al., "Conformational analysis of biantennary glycans and molecular moldeling of their complexes with lentil lectin", Journal of Molecular Graphics and Modeling, Feb. 1997, vol. 15, No. 1, pp. 37-42, 54, XP002293396 ISSN: 1093-3263.
Sparks et al., "Synthesis of potential inhibitors of hemagglutination by Influenza virus: chemoenzymic preparation of N-5 analogs of N-acetylneuraminic acid", Tetrahedron, 1993, vol. 49, pp. 1.
Spearman et al., "Production and glycosylation of recombinant â-interferon in suspension and cytopore microcarrier cultures of CHO cells", Biotechnol. Prog., 2005, vol. 21, pp. 31-39.
Sung et al., "Effect of sodium butyrate on the production, heterogeneity and biological activity of human thrombopoietin by recombinant Chinese hamster ovary cells", Journal of Biotechnology, 2004, vol. 112, pp. 232-335.
Supplemental Partial European Search Report, dated Aug. 31, 2004 for Application No. 02773390.6.
Takeuchi et al: ,"Structures and functional roles of the sugar chains of human erythropoietins", Glycobiology, 1991, vol. 1, No. 4, 337-346.
Tran et al., "Separation of carbohydrate-mediated microheterogeneity of recombinant human erythropoietin by free solution capillary electrophoresis", Journal of Chromatography, 1991, vol. 542, pp. 459-471.
Trummer et al., "Process parameter shifting: part I. Effect of DOT, pH, and temperature on the performance of Epo-Fc expressing CHO cells cultivated in controlled batch bioreactors", Biotechnol. and Bioeng., 2006, vol. 94, No. 6, pp. 1033-1044.
Umaña et al., "Engineered glycoforms of an antineuroblastoma IgG1 with optimized antibody-dependent cellular cytotoxic activity", Nature Biotechnology, 1999, vol. 17, pp. 176-180.
Varki, "Radioactive tracer techniques in the sequencing of glycoprotein oligosaccharides", J. FASEB, 1991, vol. 2, pp. 226-235.
Venkataraman et al., "Sequencing complex polysaccharides", Science, 1999, vol. 286, pp. 537-542.

Von Der Lieth, "Expanding proteomics to glycobiology: biocomputing approaches understanding the function of sugar", Pacific Symposium on Biocomputing, 2002, Abstract.
Wang et al., "EDEM an ER quality control receptor" Nat. Struct. Biol., vol. 10(5) pp. 319-321 (2003).
Watson et al.,"Capillary electrophoresis separation of human recombinant erythropoietin (r-HuEPO) glycoforms", Analytical Biochemistry, 1993, vol. 210, pp. 389-393.
Watson et al.,"Structure determination of the intact major sialylated oligosaccharide chains of recombinant human erythropoietin expressed in Chinese hamster overy cells", Glycobiology, 1994, vol. 4, No. 2, pp. 227-237.
Webb J W et al., Structural characterization of intact, branched oligosaccharides by high performance liquid chromatography and liquid secondary ion mass spectrometry Analytical Biochemistry, vol. 169, pp. 337-349 (1998).
Wong et al., "Impact of dynamic online fed-batch strategies on metabolism, productivity and N-glycosylation quality in CHO cell cultures", Biotechnol. and Bioeng., 2005, vol. 89, No. 2, pp. 164-177.
Wopereis et al., "Mechanisms in Protein O-Glycan Biosynthesis and Clinical and Molecular Aspects of Protein O-Glycan Biosynthesis Defects: A Review" Clinical Chem., vol. 52(4) pp. 547-600 (2006).
Wright et al., "In vivo trafficking and catabolism of IgG1 antibodies with Fc associated carbohydrates of differing structure", Glycobiology, 2000, vol. 10, No. 12, pp. 1347-1355.
Yang et al. "Bio-Basis Function Neural Network for Prediction of Protease Cleavage Sites in Proteins" IEEE Transactions on Neural Netwroks, vol. 16, pp. 263-274 (2005).
Yang et al., "Achievement of high cell density and high antibody productivity by a controlled-fed perfusion bioreactor process", Biotechnol. and Bioeng., 2000, vol. 69, No. 1, pp. 74-82.
Yang et al., "Effect of ammonia on the glycosylation of human recombinant erythropoietin in culture", Biotechnol. Prog., 2000, vol. 16, pp. 751-759.
Ye et al., "N-glycan branching requirement in neuronal and postnatal viability", Glycobiology, vol. 14(6) pp. 547-558 (2004).
Yoon et al., "Effect of culture pH on erythropoietin production by Chinese hamster overy cells grown in suspension at 32.5 and 37 degree Celsius", Biotechnol. and Bioeng., 2005, vol. 89, No. 3, pp. 345-356.
Yoon et al., "Effect of simultaneous application of stressful culture conditions on specific productivity and heterogeneity of erythropoietin in Chinese hamster overy cells", Biotechnol. Prog., 2004, vol. 20, pp. 1293-1296.
Yuen et al., "Relationships between the N-glycan structures and biological activities of recombinant human erythropoietins produced using different culture conditions and purification procedures", British Journal of Haematology, 2003, vol. 121, pp. 511-526.
Yuk et al., "Changes in the overall extent of protein glycosylation by Chinese hamster overy cells over the course of batch culture", Biotechnol. Appl. Biochem., 2002, vol. 36, pp. 133-140.
Yuk et al., "Glycosylation by Chinese hamster overy cells in dolichol phosphate-supplemented cultures", Biotechnol. Appl. Biochem., 2002, vol. 36, pp. 141-147.
Anulula et al., "Advances in fluorescence derivatization methods for high-performance liquid chromatographic analysis of glycoprotein carbohydrates", Analytical Biochemistry, 305(1), pp. 1-23 (2006).
Becker et al., "Fucose: biosynthesis and biological function in mammels" Glycobiology, Jul. 13(7) pp. 41R-53R (2003).
Dorka et al., "Modelliong Batch and Fed-Batch Mammalian Cell Cultures for Optimizing MAb Productivity", M.S. Thesis pp. 1-197 (2007).
Hara et al., "Determination of Mono-O-acetylated N-Acetylneuraminic Acids in Human and Rat Sera by Fluorometric High-Performance Liquid Chromatography" Analytical Biochemistry, 179 pp. 162-166 (1989).
Krapp et al., "Structural Analysis of Human IgG—Fc Glycoforms Reveals a Correlation Between Glycosylation and Structural Integrity", Journal of Molecular Biology, 325(5) pp. 979-989 (2003).

(56) References Cited

OTHER PUBLICATIONS

Schulz et al., "Mediators of galactose sensitivity in UDP=galactoe 4'-epimerase-impaired mammalian cells" J. Biol Chem, 280 (14) pp. 13493-13502 (2005).
Srinivas et al., "Pharmacokinetics and Pharmacodynamics of CTLA4Ig (BMS-188667), a Novel Immunosuppressive Agent, in Monkeys following Multiple Doses" Journal of Pharmaceutical Sciences, 85(1) pp. 1-4 (1996).
Srinivas et al., "Assessment of Dose Proportionality, Absolute Bioavailability, and Immunogenicity Response of CTLA4Ig (BMS-188667), a Novel Immunosuppressive Agent, Following Subcutaneous and Intravenous Administration to Rats" Pharmaceutical Research, 14(7) pp. 911-916 (1997).
Weiner et al., "A senstive enzyme immunoassay for the quantitation of human CTLA4Ig fusion proten in mouse serum: pharmacokinetic application to optimizing cell line selection" Journal of Pharmaceutical and Biomedical Analysis, 15(5) pp. 571-579 (1997).
C.E. Joosten et al: "Effect of Culture Conditions on the Degree of Sialylation of a Recombinant Glycoprotein Expressed in Insect Cells", Biotechnology Progress, vol. 19, No. 3, 6 pp. 739-749 (2003).
Chen P et al: "Effects of elevated ammonium on glycosylation gene expression in CHO cells", Metabolic Engineering, Academic Press, US, vol. 8, No. 2, pp. 123-132 (2006).
Cox et al: "Glycan Optimization of a Human Monoclonal Antibody in the Aquatic Plant Lemna Minor", Nature Biotechnology, Nature Publishing Group, New York, NY, US, vol. 24, No. 12, pp. 1591-1597 (2006).
Extended European Search Report dated Mar. 1, 2013.
Extended European Search Report from European application serial No. 11766762.6 dated Jan. 28, 2014.
FDA. Scientific Considerations in Demonstrating Biosimilarity to a Reference Product [online] Feb. 2012 [retrieved Dec. 10, 2013].
Fleischer Eta L., "Mechanism of Glycosylation ion the Golgi Apparatus" The Journal of Histochemistry and Cytochemistry, vol. 31, No. 8, pp. 1033-1040 (1983).
Hendrick V et al: "Increased productivity of recombinant tissular plasminogen activator (t-PA) by butyrate and shift of temperature: a cell cycle phases analysis", Cytotechnology, Kluwer Academic Publishers, DO, vol. 36, No. 1-3, pp. 71-83 (2001).
Hosoi S et al: "Modulation of Oligosaccharide Structure of a Pro-Urokinase Derivative (PRO-UKDELTAGS1) by Changing Culture Conditions of a Lymphoblastoid Cell Line Namalwa KJM-1 Adapted to Serum-Free Medium", Cytotechnology, Kluwer Academic Publishers, Dordrecht, NL, vol. 19, No. 2, pp. 125-135 (1996).
International Preliminary Report on Patentability for International Application Serial No. PCT/US2012/028759 dated Jan. 14, 2014.
International Search Report and Written Opinion for corresponding International Application Serial No. PCT/US2013/043670 dated Jan. 7, 2014.
International Search Report and Written Opinion from International Serial No. PCT/US13/43696 dated Jan. 17, 2014.
International Search Report dated Jan. 7, 2014 in PCT/US2013/43671.
International Search Report including the Written Opinion for International Application Serial No. PCT/US2013/043667 dated Jan. 13, 2014.
International Search Report including Written Opinion for International Application Serial No. PCT/US13/43676 dated Jan. 16, 2014.
International Search Report including Written Opinion for International Application Serial No. PCT/US13/43693 dated Jan. 13, 2014.
International Search Report including Written Opinion for PCT/US13/43671 dated Jan. 7, 2014.
International Search Report including Written Opinion for PCT/US2013/43674 dated Jan. 15, 2014.
International Search Report including Written Opinion for PCT/US2013/43675 dated Dec. 23, 2013.

Jabs et al. Fast and Extensive Mass Spectrometry Characterization of Theraputic mABs: The Panitumumab Case Study [online] CASSS Mass Spec Meeting Sep. 14, 2012 Poster 125 [ retrieved Dec. 10, 2013].
Jong Hyun Nam et al: "The effects of culture conditions on the glycosylation of secreted human placental alkaline phosphatase produced in Chinese hamster ovary cells", Biotechnology and Bioengineering, vol. 100, No. 6, 4, pp. 1178-1192 (2008).
Lifely M R et al: "Glycosylation and biological-activity of CAMPATH-1H expressed in different cell-lines and grown under different culture conditions", Glycobiology, Oxford University Press, US, vol. 5, No. 8, pp. 813-822 (1995).
Robinson D K et al: "Characterization of a recombinant antibody produced in the course of a high yield fed-batch process", Biotechnology and Bioengineering, Wiley & Sons, Hoboken, NJ, US, vol. 44, No. 6, 5, pp. 727-735 (1994).
Rodriguez J et al: "Enhanced production of monomeric interferon-[beta] by CHO cells through the control of culture conditions", Biotechnology Progress, American Institute of Chemical Engineers, US, vol. 21, No. 1, pp. 22-30 (2005).
Search Report from Chinese Application No. 201180022319.9 dated Sep. 30, 2102.
Sherman, MD, RE, Biosimilar Biological Products. Biosimilar Guidance Webinar. US Food and Drug Administration pp. 1-22 (2012).
Trombetta et al., "Glycoprotein reglucosylation and nucleotide sugar utlization in the secretory pathway: identification of a nucleoside diphosphatase in the endoplasmic reticulum" The EMBO Journal, vol. 18, No. 12, pp. 3282-3292 (1999).
Van Berkel et al., "N-linked glycosylation is an important parameter for optimal selection of cell lines producing biopharmaceutical human IgG", Biotechnology Progress, Vo;. 25, No. 1, pp. 244-251 (2009).
Van De Nieuwenhof et al., "Recombinant glycodelin carring the same type of glycan structures as contraceptive glycodelin-A can be produced in human kidney 293 cells but not in Chinese hamster ovary cells" Eur. J. Biochem, vol. 267 pp. 4753-4762 (2000).
Zhang et al., "Quantitative analysis and process monitoring of site-specific glycosylation microheterogeneity in recombinant human interferon-gamma from Chinese hamster ovary cell culture by hydrophilic interaction chromatography" Journal of Chromatography B: Biomedical Sciences & Applications, vol. 712, No. 1-2, pp. 73-82 (1998).
International Preliminary Report on Patentability and Written Opinion for International application No. PCT/US2010/037454 dated Dec. 6, 2011
International Preliminary Report on Patentability and Written Opinion from International Application Serial No. PCT/US2008/060365 dated Apr. 2, 2009.
Shinkawa Eta L., The absense of fucose but not the presence of galactose or bisecting N-acetylglucosamine of human IgG1 complex-type oligosaccharides shows the critical role of enhancing antibody-dependent cellular cytotoxicity. J Biol Chem., vol. 278(5) pp. 3466-3473 (2003).
Hodoniczky, et al., "Control of Recombinant Monoclonal Antibody Effector Functions by Fc N-Glycan Remodeling in Vitro" Biotechnol. Prog., 21:1644-1652 (2005).
Jefferis, "Glycosylatin of Human IgG Antibodies: Relevance to Therapeutic Applications" Biopharm. Advanstar Communications, Inc., 14(9):19-27 (2001).
Lucocq, et al., "Detection of Terminal N-Linked N-acetylglucosamine Residues in the Golgi Apparatus using Galactosyltransferase and Endoglucosaminidase F/Peptide N-glycosidase F: Adaptation of a Biomedical Approach to Electron Microscopy" The Journal of Histochemistry and Cytochemistry, 35(1):67-74 (1987).
Supplemental Partial European Search Report, dated Jan. 23, 2015 for Application No. EP 12757887.0.
Von Horsten, et al., "Production of non-fucosylated antibodies by co-expression of heterologous GDP-6-deoxy-D-lyxo-4-hexulose reductase" Glycobiology, 20(12):1607-1618 (2010).

(56) References Cited

OTHER PUBLICATIONS

Yoko-O, et al., "An N-acetylglucosaminyltransferase of the Golgi apparatus of the yeast *Saccharomyces cerevisiae* that can modify N-linked glycans" Glycobiology, 13(8):581-589 (2003).

Shields et al., "Lack of Fucose on Human IgG1 N-Linked Oligosaccharide Improves Binding to Human FcyRIII and Antibody-dependent Cellular Toxicity," The Journal of Biological Chemistry, 277(30)26733-236740(2002).

Cornil et al. Tumor cell surface beta 1-4-linked galactose binds to lectin(s) on microvascular endothelial cells and contributes to organ colonization. J Cell Bioi. Aug. 1990;111 (2):773-81.

Extended European Search Report from European Patent Application No. 12757887.0 dated May 28, 2015.

Hamid et al., "A strategy to reveal potential glycan markers from serum glycoproteins associated with breast cancer progression" Glycobiology (2008) vol. 18 No. 12 pp. 1105-1118.

Lee et al, "A mutation causing a reduced level of expression of six beta4-galactosyltransferase genes in the basis of the Lec19 CHO glycosylation mutant." Biochemistry (2003) vol. 42 No. 42 pp. 12349-12357.

Rao et al., "Influence of Glycopeptide Structure on the Regulation of Galactosyltransferase Activity" Biochemistry (1978) vol. 17 No. 26 pp. 5632-5638.

Supplemental Partial European Search Report from 10781083.0 dated Nov. 27, 2015.

Wuhrer et al., "Glycosylation profiling of immunoglobulin G (IgG) subclasses from human serum" Proteomics (2007) vol. 7 No. 22 pp. 4070-4081.

Chen et al., Mammalian Glycosylation: An Overview of Carbohydrate Biosynthesis. In: Handbook of Carbohydrate Engineering, CRC Press, Yarema, K.J., ed. 2005, Chapter 1, p. 1-48; Figure 1.3; p. 16, para 1-2.

Hara-Kuge et al., Vesicular-integral membrane protein, VIP36, recognizes hihg-mannose type glycans containing alpha1>2 mannosyl residues in MDCK cells, Glycobiology, 9(8):833-939 (1999) abstract; p. 837, para 2.

\* cited by examiner

HIGH MANNOSE GLYCANS

This application is a National Stage Application under 35 U.S.C. § 371 from PCTUS2011/031637, filed Apr. 7, 2011, which claims priority to U.S. Application Ser. No. 61/321,857, filed on Apr. 7, 2010. The disclosure of the prior application is considered part of (and is incorporated by reference in) the disclosure of this application.

BACKGROUND OF THE INVENTION

A typical glycoprotein product differs substantially in terms of complexity from a typical small molecule drug. The sugar structures attached to the amino acid backbone of a glycoprotein can vary structurally in many ways including, sequence, branching, sugar content, and heterogeneity. Thus, glycoprotein products can be complex heterogeneous mixtures of many structurally diverse molecules which themselves have complex glycan structures. Glycosylation adds not only to the molecule's structural complexity but affects or conditions many of a glycoprotein's biological and clinical attributes.

SUMMARY OF THE INVENTION

The invention is based, at least in part, on methods and compositions related to the analysis and control of high mannose glycan structures (Man4, Man5, Man6, Man7, Man8 and/or Man9 structures) on glycoproteins. The N-linked glycan pathway showing the synthesis of high mannose and complex glycan structures, is shown in FIG. 1.
Product Analytical Methods Accordingly, in some aspects, the invention features methods to analyze high mannose structures on a glycoprotein preparation, e.g., methods to identify and/or quantify high mannose glycans or glycoforms. Such methods can be used to measure one or more of: the presence and/or amount of high mannose in a glycan or glycoprotein preparation (e.g., relative to total glycan mass); the relative ratios of high mannose structures [e.g., relative ratios of high mannose species to each other (e.g., relative abundances or ratios of Man4, Man5, Man 6, Man7, Man8 and/or Man9 and isomers thereof), relative ratios of high mannose to hybrid structures, relative ratios of high mannose to complex structures, relative ratios of high mannose to fucosylated structures]; the presence or abundance of modified high mannose structures (e.g., the presence or abundance of fucosylated high mannose structures).

In one such aspect, the invention features a method to analyze (identify and/or quantify) high mannose glycoforms in a glycoprotein mixture, e.g., a glycoprotein preparation. The method includes: (a) providing a glycoprotein-containing sample; (b) optionally performing a buffer exchange to buffer compatible with enzymatic digest and/or mass spectrometry (MS) analysis, (c) removing higher abundance glycans from the glycoprotein sample (e.g., treating the glycoprotein sample with an enzyme that cleaves complex fucosylated glycans from the glycoprotein, e.g., treating with Endoglycosydase F3); (d) optionally reducing and alkylating the sample and/or performing a buffer exchange to buffer compatible with mass spectrometry. In one embodiment, a next step (e) includes identifying and/or quantifying high mannose-containing glycoforms in the treated sample (e.g., by electrophoretic methods such as capillary electrophoresis (CE); reverse phase LC-MS or targeted reverse phase-LC-MS). In certain embodiments in which the theoretical masses of the high mannose-containing glycoforms are known, a targeted MS experiment can be established to only monitor selected set of m/z signatures corresponding to these species. In another embodiment, step (e) alternatively includes identifying and/or quantifying low abundance glycoforms in the treated sample, including but not limited to high mannose glycoforms.

In one embodiment the method is a high resolution method, e.g., the method separately identifies and/or quantifies individual glycoforms (e.g., at least 1, 2, 3, 4, 5, 6, 7, 8, 9, individual glycoforms) in a glycoprotein mixture.

In one embodiment the glycoprotein mixture is an antibody preparation, e.g., a pharmaceutical antibody preparation. In one embodiment, the antibody preparation was expressed from a mammalian cell culture.

In another such aspect, the invention features a method to analyze (identify and/or quantify) high mannose and/or hybrid structures in a glycan or glycoprotein preparation. The method includes (a) providing a glycan or glycoprotein mixture, (b) treating the glycan mixture or glycoprotein mixture with an enzyme that cleaves the exposed terminal mannosidase residues at the non-reducing end of a glycoform, and (c) quantifying the cleaved terminal mannose residues. In one embodiment, the quantifying step includes performing quantitative monosaccharide analysis (e.g., by HPLC or GC-MS). In an embodiment, the released terminal mannoses are quantified relative to total glycan mass, thereby analyzing high mannose and/or hybrid structures in a glycan or glycoprotein preparation.

In one embodiment the glycoprotein preparation is an antibody preparation, e.g., a pharmaceutical antibody preparation. In one embodiment, the antibody preparation was expressed from a mammalian cell culture.

In some embodiments, an analytical method described herein detects high mannose structures present at low abundance in a glycoprotein preparation, e.g., the method detects high mannose structures, e.g., one or more of Man4, Man5, Man 6, Man7, Man8 and/or Man9, present at less than 20%, 15%, 10%, 9%, 8%, 7%, 6%, 5%, 4%, 3%, 2%, 1%, 0.5%, 0.3%, 0.1% or less than 0.05% abundance relative to total glycan mass.

In some embodiments, the method is a high-throughput method, e.g., all the steps of the method can be completed in less than 8, 7, 6, 5, 4, 3, 2 hours per sample; the method can be used to process at least 5 samples per day. In another embodiment, greater than 20, 30, 40, 50, 60, 70, 80, 90 or 100 samples can be run per day using one operator and one instrument per method. In another embodiment, the method requires minimal sample preparation (e.g., sample preparation includes only an optional buffer exchange; does not require multiple clean-up or purification steps, and/or or derivatization procedures).

In one embodiment, the method is a method run under GMP conditions.

In one embodiment, the glycoprotein is an immunoglobulin (IgG) (e.g., a therapeutic antibody such as an IgG1, IgG2) or an Ig fusion (e.g., a therapeutic receptor-Fc fusion). Some examples include: bevacizumab, tositumomab, abciximab, alemtuzumab, acritumomab, cetuximab, adalimumab, ranibizumab, gemtuzumab, efalizumab, infliximab, abciximab, rituximab, basiliximab, eculizumab, palivizumab, omalizumab, daclizumab, ibritumomab tiuxetan, certolizumab pegol, daclizumab, eculizumab, muromonab-CD3, natalizumab, panitumumab, ranibizumab, tositumomab, alefacept, etanercept, abatacept.

In other embodiments, the glycoprotein is a therapeutic hormone (e.g., FSH), an interferon, an erythropoietin, a colony stimulating factor, or a therapeutic replacement enzyme (e.g., glucocerebrosidase, alpha-galactosidase).

Methods of the present disclosure may be used for assessment of high mannose structures in one or more stages of development in the production of a therapeutic or other commercially relevant glycoprotein, for example, during host cell selection, clonal selection, media optimization, determination of culture conditions, process conditions, and/or purification procedures.

Methods disclosed herein can also be utilized to monitor the extent and/or type of high mannose glycans produced in a cell culture, thereby allowing adjustment or possibly termination of the culture in order, for example, to achieve a particular desired high mannose pattern or target or to avoid development of a particular undesired high mannose pattern or target. In some embodiments, the methods can be utilized to compare the extent and/or type of high mannose glycosylation occurring in different cell cultures. In some embodiments, methods may be used to monitor the glycosylation pattern of glycoproteins produced during the course of their production by cells. For example, production of a glycoprotein (e.g., commercial production) may involve steps of (1) culturing cells that produce the glycoprotein, (2) obtaining samples at regular or irregular intervals during the culturing, and (3) analyzing the glycosylation pattern of produced glycoprotein(s) in obtained samples. In some embodiments, such methods may comprise a step of comparing the glycosylation patterns of produced glycoproteins in obtained samples to one another. In some embodiments, such methods may comprise comparing the glycosylation patterns of produced glycoproteins in obtained samples to the glycosylation pattern of a reference sample (such as a control sample or a GMP or pharmaceutical specification or standard).

The disclosed methods can also be utilized to assess high mannose glycosylation characteristics of cells or cell lines that are being considered for production of a particular desired glycoprotein (for example, even before the cells or cell lines have been engineered to produce the glycoprotein, or to produce the glycoprotein at a commercially relevant level).

Methods of the present disclosure can be applied to glycans or glycoproteins obtained from a wide variety of sources including, but not limited to, therapeutic formulations and biological samples. A biological sample may undergo one or more analysis and/or purification steps prior to or after being analyzed according to the present disclosure. Methods of the present disclosure can be utilized to analyze glycans in any of a variety of states including, for instance, free glycans, glycoconjugates (e.g., glycopeptides, glycolipids, proteoglycans, etc.), cell-associated glycans (e.g., nucleus-, cytoplasm-, cell-membrane-associated glycans, etc.); glycans associated with cellular, extracellular, intracellular, and/or subcellular components (e.g., proteins); glycans in extracellular space (e.g., cell culture medium), etc.

In some embodiments, a desired high mannose glycosylation pattern for a particular target glycoprotein is known, and the methods described herein allow monitoring of culture samples to assess progress of the production along a route known to produce the desired pattern. For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible, whether or not it is being produced by exactly the same route. In such embodiments, samples of the production culture are typically taken at multiple time points and are compared with an established standard or with a control culture in order to assess relative glycosylation. Among other things, the present disclosure can facilitate real time analysis of high mannose glycosylation in production systems for therapeutic proteins.

The methods described herein can also be used to assess, control and/or compare the quality of therapeutic products, e.g., to assess the presence, amounts, ratios and/or species of high mannose structures in a therapeutic or otherwise commercially relevant glycoprotein product. For example, the methods can be used in a quality control assay or API or drug product release assay, for example, the methods can include a step of releasing a glycoprotein product for pharmaceutical use if the product meets a control or reference specification for high mannose structures. The reference level can be a specification (e.g., a GMP standard, an FDA label or Physician's Insert) or quality criterion for a pharmaceutical preparation containing the glycoprotein composition. In other embodiments, a comparison is with a historical record of a prior or standard batch and/or with a reference sample of glycoprotein. Features of the analysis can be recorded, for example in a quality control record (e.g., a certificate of testing or a certificate of analysis).

In some embodiments, the reference level or quality criterion is no more than 20%, 15%, 12%, 10% high mannose structures present in a glycoprotein composition, e.g., no more than 9%, 8%, 7%, 6%, 5%, 4%, 3%, 2%, 1%, 0.5%, 0.25%, 0.2%, 0.1% or 0.05%. In one embodiment, the glycoprotein has high mannose structures (e.g., has at least 0.01%, 0.05% or 0.1% high mannose) but has no more than 10%, 9%, 8%, 7%, 6%, 5%, 4%, 3%, 2%, 1%, 0.5%, 0.25%, 0.2%, 0.1% or 0.05%, e.g., has between 0.05-20% high mannose, 0.05-15% high mannose 0.05-10% high mannose, between 1-10% high mannose, between 1-5% high mannose. The level of high mannose structures present in a glycoprotein composition can be generally measured as the level of glycans containing high mannose structures relative to total amount of glycans in a sample, such as a glycoprotein preparation.

In some embodiments, a desired high mannose glycosylation pattern will be enriched for a particular structure. For example, in some embodiments, a desired glycosylation pattern will have lower levels (e.g., less than about 20%, about 15%, about 10%, about 8%, 7%, 6%, 5%, 4%, 3%, 2%, 1%, 0.5%, 0.2%, 0.1% or less) of high mannose structures, or high levels (e.g., greater than about 5%, 10%, 20%, 25%, 30%, 40%, 50%) of high mannose structures, or specified levels of Man4, Man5, Man 6, Man7, Man8 and/or Man9 (e.g., enrichment of Man5 and/or Man8 relative to other high mannose species or relative to total glycan mass).

Cellular-Based Analytical Methods

It has been found that multiple cellular pathways interact to determine the pattern of high mannose glycans present on glycoproteins produced from a particular cell. It has been found that the pattern of high mannose glycans on a glycoprotein made by a cell will depend on the balance and patterns of formative vs. consumptive components described herein (e.g., expression of certain genes and availability of certain metabolites described herein) unexpectedly related to biosynthesis of high mannose structures. The patterns of expression or availability of such components in a cell or cell population is indicative or predictive of the pattern of high mannose structures produced by the cell or cell population, e.g., is indicative or predictive of the high mannose content of a therapeutic glycoprotein produced by such cell or cell population.

Accordingly, in another aspect, the invention features a method of evaluating a cell's ability and/or potential to produce high mannose structures. The method includes: providing a cell, and evaluating two or more (e.g., 3 or more, 4 or more, 5 or more, 6 or more, 7 or more, 8 or more, 9 or more, or 10 or more) components of the cellular machinery described herein, wherein the result of the evaluation is indicative of the high mannose glycan pattern present in a glycoprotein produced by the cell.

In one embodiment, the components of the cellular machinery are selected from:
Glycosyltransferases/Enzymes
   MGAT1 (GlcNAc T1);
   Alpha mannosidase II, IIx;
   Alpha mannosidase IB;
   Alpha mannosidase IA;
   FucT1-9;
   Glucosidase (e.g., GCS1, GANAB).
Precursor Levels
   UDP-GlcNAc
   GDP-Man
   UDP/UTP
   GDP/GTP
   Uridine
   Guanosine
Precursor Biosynthesis or Localization or Trafficking
   GNE (glucosamine (UDP-N-acetyl)-2-epimerase/N-acetylmannosamine)
   Golgi UDP phosphatase
   UDP-GlcNAc transporter
   UAP-1 (UDP-N-acetylhexosamine pyrophosphorylase)
   PGM-3—phosphoglucomutase 3
   NAGK—N-acetyl-D-glucosamine kinase
   GNPNAT1—glucosamine-phosphate N-acetyltransferase 1
   UGP-2—UDP-glucose pyrophosphorylase 2
   UGDH—UDP-glucose 6-dehydrogenaseGAlK-1—Galactokinase-1
   PGM-1—Phosphoglucomutase-1
   GCK—Glucokinase
Targets to Alter the Localization or Trafficking Through the ER and Golgi
   Chaparones (BiP, SNARE, cpn's, hsp's)
   EDEM (ER degrading mannosidase-like protein)
   MANEA
   Mannose receptor
   Golgi architecture, structural
   Golgi lipid content (sphingolipid, cholesterol content)
   Trafficking components (A1P1, VIP36)

In one embodiment, the ratio of expression of MGAT1 to alpha mannosidase IB is evaluated. A low ratio, e.g., less than 1, indicates that the levels of Man5 in a glycoprotein produced by the cell will be elevated relative to the total glycan pool.

In one embodiment, the ratio of MGAT1 to alpha mannosidase IA is evaluated. A low ratio, e.g., less than 1, indicates that the levels of Man5 in a glycoprotein produced by the cell will be elevated relative to the total glycan pool In one embodiment, the ratio of expression of MGAT1 to MGAT2 is evaluated. A low ratio, e.g. less than 1, indicates that the levels of Man5 in a glycoprotein produced by the cell will be elevated relative to the total glycan pool.

In one embodiment, the ratio of expression of NAGK/GNE and/or NAGK to MGAT2 is evaluated. A low ratio of both, e.g. each less than 1, indicates that the levels of high mannose structures will be elevated relative to the total glycan pool In one embodiment, the ratio of expression of MGAT1 to glucosidase is evaluated. A low ratio, e.g. less than 1, indicates that the levels of certain high mannose structures (Man5, Man6, Man7, Man8, and or Man9) will be elevated relative to the total glycan pool.

In one embodiment, the ratio of expression of Mannosidase IA and IB is evaluated. Differences in ratio of expression of these can affect the composition of high mannose structures (e.g., Man8 and Man9 in particular) present on a glycosylated protein.

In one embodiment, the ratio of expression of EDEM and mannosidase IA is evaluated. A high ratio, e.g., greater than 1, would indicate a bias toward high mannose in a glycoprotein produced in a cell.

In one embodiment, the ratio of expression of Mannosidase IIx and MGAT1 is evaluated. A high ratio, e.g., greater than 1, indicates a bias toward lower mannose in a glycoprotein produced in a cell.

In one embodiment, the ratio of expression of Mannosidase IA and a 1,3 glucosidase (GANAB) is evaluated. A high ratio, e.g., greater than 1, would indicate a bias toward high mannose (e.g., Man9) in a glycoprotein produced in a cell.

In one embodiment, the ratio of a fucosyl transferase to mannosidase 1b is evaluated. A low ratio, e.g., less than 1, indicates an enrichment in high mannose, e.g., Man5.

In one embodiment, the ratio of expression of Mannosidase II to Mannosidase IB is evaluated. A low ratio, e.g., less than 1, indicates enrichment in high mannose, e.g., Man5.

In one embodiment, the level of VIP36 expression is evaluated. Expression levels of VIP36 influence the mannose content of glycoproteins produced in the cell. In one embodiment, the ratio of expression of VIP36 and Mannosidase IA is evaluated. In one embodiment, the ratio of expression of VIP36 and mannosidae IB is evaluated.

In one embodiment, the level of UGP-2 is evaluated. Expression levels of UGP-2 influence the mannose content of glycoproteins expressed in the cell. In one embodiment, the ratio of expression of UGP-2 to Mannosidase IB is evaluated. A high ratio (e.g. greater than one) would indicate a higher level of high mannose structures.

In some embodiments, the method further includes selecting a cell as a host cell for expression of a therapeutic glycoprotein (such as an IgG molecule) based on the result of the method of evaluating a cell's ability and/or potential to produce high mannose structures. For example, in one embodiment the cell is selected as a host cell if the result of the method of evaluating the cell's ability and/or potential to produce high mannose structures indicates that the cell can or will produce a glycoprotein having low levels of high mannose structures (e.g., <20%, <15%, <10%, <9%, <8%, <7%, <6%, <5%, <4%, <3%, <2%, <1%, <0.5% high mannose structures relative to total glycan mass). In another example, in one embodiment the cell is selected as a host cell if the result of the method of evaluating the cell's ability and/or potential to produce high mannose structures indicates that the cell can or will produce a glycoprotein having higher levels of high mannose structures (e.g., >10%, >15%, >20%,) high mannose structures relative to total glycan mass). In another example, in one embodiment the cell is selected as a host cell if the result of the method of evaluating the cell's ability and/or potential to produce high mannose structures indicates that the cell can or will produce a glycoprotein having a predetermined high mannose structure (e.g., a predetermined relative ratio of one high mannose species to another, e.g., relative abundances or ratios of Man4, Man5, Man 6, Man7, Man8 and/or Man9 and isomers thereof; predetermined relative ratios of high mannose to hybrid structures; predetermined relative ratios of high mannose to complex structures; predetermined relative ratios of high mannose to fucosylated structures; predetermined abundance of modified high mannose structures (e.g., fucosylated high mannose structures)

In one embodiment, the method further includes a step of genetically engineering the selected cell to express a therapeutic glycoprotein, e.g., a therapeutic IgG based molecule, e.g., a therapeutic antibody or receptor-Fc fusion protein, e.g., bevacizumab, tositumomab, abciximab, alemtuzumab, acritumomab, cetuximab, adalimumab, ranibizumab, gemtuzumab, efalizumab, infliximab, abciximab, rituximab, basiliximab, eculizumab, palivizumab, omalizumab, daclizumab, ibritumomab tiuxetan, certolizumab pegol, daclizumab, eculizumab, muromonab-CD3, natalizumab, panitumumab, ranibizumab, tositumomab, alefacept, etanercept, abatacept.

In some embodiment, the method further includes expressing and harvesting the glycoprotein from the genetically engineered cell and evaluating high mannose structures of the produced glycoprotein, e.g., using a method described herein.

Methods to Control High Mannose Structures

Methods to modulate high mannose structures have been developed. Accordingly, in one aspect, the invention features a method for modulating the glycan structure of a glycoprotein, e.g., a recombinant therapeutic glycoprotein, e.g., modulating the amount or pattern of high mannose structures present in a recombinant therapeutic glycoprotein or otherwise commercially relevant glycoprotein. The method includes (a) providing a host cell genetically engineered to express a subject glycoprotein, and (b) culturing the cell under conditions to express the recombinant protein, wherein the host cell is subject to a manipulation that modulates one or more, e.g., two or more (e.g., 3 or more, 4 or more, 5 or more, 6 or more, 7 or more, 8 or more, 9 or more, or 10 or more) components of the cellular machinery described herein to thereby modulate the high mannose glycan structure of a glycoprotein. In some embodiment, high mannose content is evaluated during culturing and/or at or after harvest of the cells.

In one embodiment, the host cell is subject to a manipulation that modulates a glycosyltransferase described herein (e.g., MGAT1). In one embodiment, the glycotransferase expression is decreased but not abolished, e.g., the glycotransferase expression is decreased by 10%, 20%, 30%, 40%, 50%, 60%, 70%, 80%, or 90% relative to a parent cell. In some embodiments, this is accomplished by use of: siRNA, antisense RNA, targeted knockout, targeted mutation, modulation of concentration of a divalent cation (e.g., Mn++, Mg+, Co++ or Zn++), modulation of ammonia, elevated pH (e.g., using ulinastatin or chloroquin), chemical inhibitors (such as: Castanospermine, Deoxynojirimycin, Deoxymannojirimycin, Australine, 2,5-Dihydroxymethyl-3,4 Dihydroxypyrrolidine, Kifunensine, Swainsonine, Mannostatin A, 1,4-Dideoxy-1,4-Imino-D-Mannitol); modulation (e.g., addition) of oleic acid, modulation (e.g., addition) of retinoic acid, modulation of transcription factors (e.g., RFX1, Pax-4-a, CHOP-10, COUP-TF1, MIF-1, Evi-1, MZF-1, STAT-6, Elk-1, MAZR).

In one embodiment, the method includes supplementing the cell culture media with a divalent cation, e.g., manganese (Mn++), e.g., $MnCl_2$ (e.g., from 25-250 uM $MnCl_2$, from 25-150 uM $MnCl_2$, 25-100 uM $MnCl_2$, 25-75 uM $MnCl_2$, or 25-50 uM $MnCl_2$). In this embodiment, the method increases the levels of high mannose in a preparation of the glycoprotein produced by the cell, e.g., increases the level of HM5. In one embodiment, the level increases by at least 10%, 20%, 25%, 30%, 40%, 50% or more, relative to the glycoprotein produced by a same host cell cultured in a same media not supplemented with Mn++. In one embodiment, the method also increases the level of afucosylated species of the glycoprotein, e.g., increases the ratio of afucosylated species relative to fucosylated species in a preparation of the glycoprotein produced by the cell. This embodiment may also include a step of measuring the level of high mannose in the glycoprotein, e.g., the total level of high mannose species or the level of one or more of HM4, HM5, HM6, HM7, HM8, HM9, or ratios thereof, This embodiment may also include a step of measuring the level of fucosylation in the glycoprotein, e.g., the total level of afucosylated species or the ratio of afucosylated to fucosylated species in a preparation of the glycoprotein produced by the cell.

In one embodiment, the method includes obtaining or determining the identity or quantity of a high mannose glycoform in a glycoprotein sample, e.g., by a method described herein, and supplementing the cell culture media with a divalent cation, e.g., manganese (Mn++), e.g., $MnCl_2$ (e.g., from 25-250 uM $MnCl_2$, from 25-150 uM $MnCl_2$, 25-100 uM $MnCl_2$, 25-75 uM $MnCl_2$, or 25-50 uM $MnCl_2$), to thereby increase the levels of high mannose in a preparation of the glycoprotein produced by the cell, e.g., increases the level of HM5. In one embodiment, the level increases by at least 10%, 20%, 25%, 30%, 40%, 50% or more, relative to the glycoprotein produced by a same host cell cultured in a same media not supplemented with Mn++. In one embodiment, the method includes supplementing the cell culture media with a divalent cation, e.g., manganese (Mn++), e.g., $MnCl_2$ (e.g., from 25-250 uM $MnCl_2$, from 25-150 uM $MnCl_2$, 25-100 uM $MnCl_2$, 25-75 uM $MnCl_2$, or 25-50 uM $MnCl_2$), obtaining or determining the identity or quantity of a high mannose glycoform, e.g., by a method described herein, in a glycoprotein sample, comparing the identity or quantity of the high mannose glycoforms to the identity or quantity of a reference sample (e.g., a control sample or a GMP or pharmaceutical specification or standard), and making a decision regarding the glycoprotein, e.g., a decision described herein.

In one embodiment, the method also increases the level of afucosylated species of the glycoprotein, e.g., increases the ratio of afucosylated species relative to fucosylated species in a preparation of the glycoprotein produced by the cell. This embodiment may also include a step of measuring the level of high mannose in the glycoprotein, e.g., the total level of high mannose species or the level of one or more of HM4, HM5, HM6, HM7, HM8, HM9, or ratios thereof, This embodiment may also include a step of measuring the level of fucosylation in the glycoprotein, e.g., the total level of afucosylated species or the ratio of afucosylated to fucosylated species in a preparation of the glycoprotein produced by the cell.

In an embodiment the level of high mannose is increased by decreasing the expression of a gene disclosed herein, e.g., MGAT1, wherein expression is decreased by a method or agent which results in a nonlinear relationship between the reduction of expression of the gene, e.g., MGAT1, and increase in high mannose. In an embodiment a plot of the reduction in expression, e.g., of MGAT1, and the increase in high mannose has essentially three phases: a phase where reduction in expression has little or no effect on the level of high mannose (it does not substantially increase high mannose), a phase in which the reduction in the level of expression is essentially linear with the increase in high mannose, and a phase where further reduction in gene expression results in little or no further increase in high mannose. In an embodiment, in a method of increasing high mannose, the level of gene expression, e.g., MGAT1 expression, is in the linear phase. In an embodiment the reduction is in the half of the linear phase just before maximal and non-linear phase. In an embodiment the reduction is in the last 25, 10, 5, or 1% of the linear phase just before maximal and non-linear phase. In an embodiment the level of reduction is no more than 1.5, 2.0 or 4.0 fold greater than the level of reduction of gene expression at the inflexion point between the linear phase and the phase where further reductions in gene expression to not give further significant increase in high mannose.

In one embodiment, the host cell is subject to a delayed or late stage harvest. In some embodiments this includes delaying the harvest until the viability of the cells is less than 40%, 30%, 20% or 10%. In other embodiments this will involve delaying the harvest until the cell number is greater than $6 \times 10^6$, $7 \times 10^6$, $8 \times 10^6$, $10 \times 10^6$, or $15 \times 10^6$ cells/ml. In other embodiments a delayed harvest may refer to but would not be limited to harvesting once the levels of media components reach a target level such as less than 70%, 60%, 50%, 40%, 30%, 20%, 10%, 5%, 2%, or 0% of the starting levels. These media components may include, but would not be limited to glucose, galactose, glutamine, or amino acid levels. In other embodiments a delayed harvest may refer to but would not be limited to harvesting once the levels of a cellular biproduct reached a target level such as greater than 2, 4, 6, 8, of 10 fold increase in the starting levels. These biproducts may include but would not be limited to ammonia and lactate. In other embodiments a delayed harvest may refer to delaying the timing of a harvest as compared to an existing feed protocol. This may involve but not be limited to delaying the harvest time for 6, 12, 18, 24, 48, 72, or 96 hrs from the existing process. In other embodiments a delayed harvest may refer to delaying the timing of a harvest until a gas consumption value is met. This may include but not be limited to delaying the harvest time until the level of oxygen consumption is greater than 50, 100, 150, 200, 250, 300, or 350 mmol/L. In other embodiments a delayed harvest may refer to delaying the harvest until a multiple of one, two, three, or four of above parameters are met. In other embodiments a delayed harvest may refer to delaying the harvest until a ratio of two of the above parameters is met. This may include but not be limited to a ratio of Lactate/Glucose that is less than 2, 1, 0.5, 0.25 or 0.1. Alternatively, this may include but not be limited to a ratio of the Oxygen/glucose that is greater than 3, 4, 5, 6, or 7.

In one embodiment, the host cell is subject to a delayed feed strategy. In some embodiments a delayed feed strategy may refer but would not be limited to postponing the addition of fed nutrients (e.g. glucose, galactose, amino acids, vitamins, phosphate components etc.) in a fed batch or perfusion culture system until the cell viability is less than 90%, 80%, or 70%, or until the cells reach a particular cell density, such as more than $5 \times 10^6$, $6 \times 10^6$, $7 \times 10^6$, $8 \times 10^6$, $10 \times 10^6$ cells/ml. In other embodiments a delayed feed strategy may refer to but would not be limited to the addition of fed nutrients once the levels of media components reach a target level such as less than 70%, 60%, 50%, 40%, 30%, 20%, or 10% of the starting levels. These media components may include, but would not be limited to glucose, galactose, glutamine, or amino acid levels. In other embodiments a delayed feed strategy may refer to but would not be limited to the addition of fed nutrients once the levels of cellular biproduct reach a target level such as greater than 2, 4, 6, 8, of 10 fold increase in the starting levels. These biproducts may include but would not be limited to ammonia and lactate. In other embodiments a delayed feed strategy may refer to delaying the start of timing of a feed strategy as compared to an existing feed protocol. This may involve but not be limited to delaying the initial start time of feed for 6, 12, 18, 24, 48, 72, or 96 hrs from the start of feed in an existing process. In other embodiments a delayed feed strategy may refer to delaying the timing of the subsequent feeds as compared to an existing feed protocol. This may involve but not be limited to delaying each subsequent feed time 6, 12, 18, 24, 48, 72, or 96 hrs from the prior feed point. In other embodiments a delayed feed strategy may refer to delaying the timing of a feed until a gas consumption value is met. This may include but not be limited to delaying the feed until the level of oxygen consumption is greater than 10, 25, 50, 100, 150, 200, 250, 300, or 350 mmol/L. In other embodiments a delayed feed strategy may refer to delaying the timing of feed until a multiple of 2, 3, or 4 of the above parameters are met. In other embodiments a delayed feed may refer to delaying the feed until a ratio of two of the above parameters is met. This may include but not be limited to a ratio of Lactate/Glucose that is less than 2, 1, 0.5, 0.25 or 0.1. Alternatively, this may include but not be limited to a ratio of the Oxygen/glucose that is greater than 3, 4, 5, 6, or 7.

In another embodiment, the host cell is subject to a manipulation that modulates Golgi architecture, e.g., manipulation (e.g., addition to cell culture) of Brefeldin A, Mycophenolic acid, Destruxin B, Concanamycin B, Leucinostatin A, Efrapeptins.

In another embodiment, the host cell is subject to a manipulation that modulates Golgi trafficking (e.g., a modulation (e.g., addition to cell culture) of components that affect budding of one Golgi compartment to another). These include Brefeldin A, Mycophenolic acid, Destruxin B, Concanamycin B, Leucinostatin A, Efrapeptins.

In another embodiment, the host cell is subject to a manipulation that modulates metabolite or precursor levels, e.g., modulation (e.g., addition to cell culture) of Galactose, 3'F UMP, UDP dialdehyde, UDP, UTP, UDP N-acetylmuramic acid, 5' aminooxy-uridine, 5'-Aminooxy-Glycyl-uridine, ManNAc. Such agents can be naturally occurring or non-naturally occurring derivatives. These may also include targeted manipulation of levels or activities of enzymes involved in the biosynthesis of the metabolites or precursors. These may include but should not be limited to those described above (e.g. GNE, UAP-1, PGM-3, NAGK, GNPNAT1, UGP-2, UGDH, GALK-1, PGM-1, GCK, Golgi UDP phosphatase, UDP-GlcNAc transporter). Mechanisms to manipulate enzyme levels include, targeted mutagenesis, siRNA, antisense RNA, targeted knockouts, and structural natural and normatural analogs.

In another embodiment, the host cell is subject to a manipulation that modulates the lipid content of the Golgi such as the addition of inhibitors or sphingolipid biosynthesis (e.g. fumonisin B1, fumonisin B2, L-cycloserine, DL-PDMP, DL-PPMP, DL-threo-dihydroshingpsine, Myriocin, L-erythro MAPP, 3-O-methylsphingomylin, N-butyldeoxynojirimycin, or Oleylethanolamide). In another embodiment the host cell is subjected to manipulation that modulates the levels of cholesterol such as the addition of an inhibitor of cholesterol biosynthesis (such as isopentenyl pyrophosphate, ezetimibe, simvastatin, inhibitors or HMG- CoA reductase) or the addition of a cholesterol sequestering agent such as Methyl-β-cyclodextrin.

In another embodiment the host cell is subjected to manipulation of levels of enzymes involved in the biosynthesis of the lipid. These enzymes can be found as described in *Molecular Biology of the Cell*, Alberts, Bray, Lewis, Raff, Robers, and Watson eds (1994). Mechanisms to manipulate enzyme levels include targeted mutagenesis, siRNA, antisense RNA, targeted knockouts, and structural and normatural analogs.

In another embodiment, the host cell is subject to a manipulation that modulates the binding affinity of L-type lectins present in the ER or Golgi (e.g., VIPL VIP36) for high mannose intermediates in the glycosylation pathway through changes in intracompartmental pH (e.g., using ulinastatin or chloroquin In another embodiment, the host cell is subject to manipulation that modulates "quality control" components involved in glycosylation and protein folding such as EDEM, MANEA, GCS1.

In another embodiment, the host cell is subject to manipulation that modulates the intracellular distribution (e.g., the localization of these enzymes preferentially to either the ER or Golgi) of mannosidase 1a and 1b.

In another embodiment, the host cell is subjected to manipulation that modulates the expression level of the protein that contains the high mannose structure (e.g. an antibody). This may be through addition of agents to acetylate chromatin (e.g. butyrate). Additionally this may be by increasing the number of genetic copies of the gene expressing the protein (e.g. antibody, e.g. through dhfr amplification, through targeted insertion, through viral insertion, through promoter sequences). In other embodiments this may be through increasing the rate of transcription or translation of the protein (e.g. antibody, e.g. through enhancer sequences, through codon optimization, promoter sequences)

In one embodiment, the method includes a step of measuring high mannose content or patterns at one or more of: before and/or after the manipulation; during culturing of the cells, after harvest of the cells, after purification of the glycoprotein.

In certain embodiment, the method includes a step of determining a desired or target level of high mannose content before manipulation. The target or desired level may be, e.g., >20%, >30%, >40%. The target or desired level may be, e.g., <20%, <15%, <10%, <8%, <7%, <6%, <5%, <4%, <3%, <2%, <1%, <0.5%. The target or desired level may be, e.g., enriched or increased levels of Man4, Man5, Man6, Man7, Man8, or Man9. This determination may include but not be limited to measuring the levels of high mannose on a reference compound, or be determined based on a desired biology, structural consideration, or by consultation of literature.

Other features and advantages of the invention will be apparent from the following detailed description, and from the claims.

DETAILED DESCRIPTION

Definitions

Figure 1:
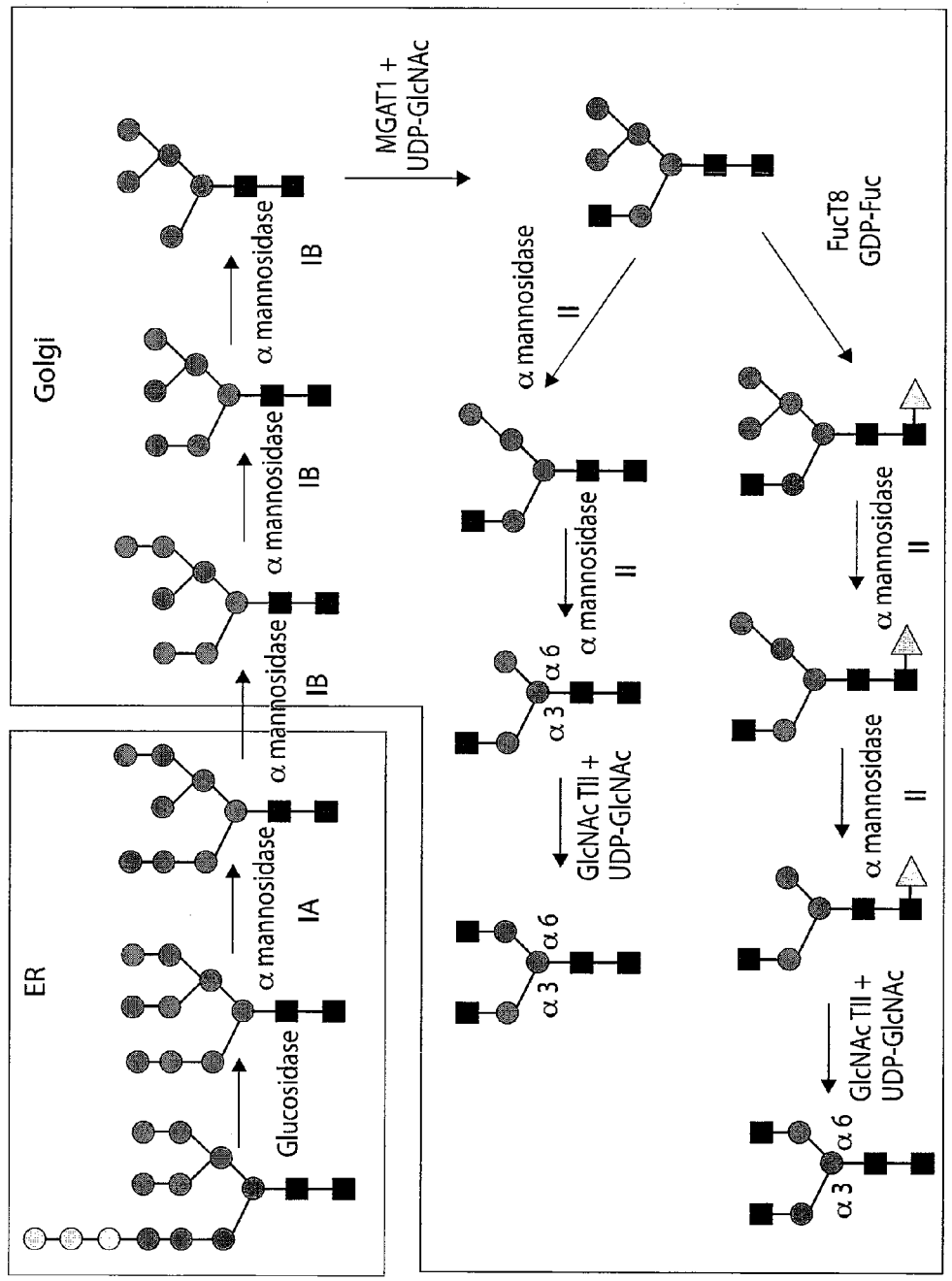
FIG. 1 is a cartoon of the pathway for biosynthesis of high mannose and complex glycans. The monosaccharides that compose the N-glycan are illustrated as the following; Fucose (light grey triangle), GlcNAc (black square), Mannose (dark grey circle), and Galactose (light grey circle). The structures that represent the high mannose species are indicated as HM9, HM8, etc.

"High Mannose" as used herein refers to one or a multiple of N-glycan structures including HM4, HM5, HM6, HM7, HM8, and HM9 containing 3, 4, 5, 6, 7, 8, or 9 mannose residues respectively. Alternatively these may be called Man4, Man5, Man6, Man7, Man8, Man9 These structures are illustrated in FIG. 1 as indicated.

A "preparation of cells", as used herein, refers to an in vitro preparation of cells. In the case of cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

The term "genetically engineered," as used herein in reference to cells, is meant to encompass cells that express a particular gene product following introduction of a heterologous DNA molecule into the cell. The heterologous DNA can be a sequence encoding the gene product and/or including regulatory elements that control expression of a coding sequence (e.g., of an endogenous sequence) for the gene product. The DNA molecule may be introduced by gene targeting or homologous recombination, i.e., introduction of the DNA molecule at a particular genomic site.

The disclosure of WO 2008/128227 is incorporated herein in its entirety. Various aspects of the invention are described in further detail below.

Host Cells/Genetically Engineered Cells

A host cell used to produce a glycoprotein described herein can be any cell containing cellular machinery to produce high mannose structures. For example, insect cells, plant cells, yeast, or mammalian cells (such as murine, human or CHO cells). CHO cells useful as host cells include cells of any strain of CHO, including CHO K1 (ATCC CCL-61), CHO pro3-, CHO DG44, CHO-S, CHO P12 or the dhfr-CHO cell line DUK-BII (Chassin et al., PNAS 77, 1980, 4216-4220). Murine cells useful as host cells include strains of NS0 or other hybridoma cell types, or similar rodent cells of BHK. Human cells useful as host cells include strains of PerC6, hybridoma cells, or retinal cells to name a few.

Suitable mammalian cells include any normal mortal or normal or abnormal immortal animal or human cell, including: monkey kidney CV1 line transformed by SV40 (COS-7, ATCC CRL 1651); human embryonic kidney line (293

(Graham et al., J. Gen. Virol. 36:59 (1977)); baby hamster kidney cells (BHK, ATCC CCL 10); Chinese Hamster Ovary (CHO), e.g., DG44, DUKX-V11, GS-CHO (ATCC CCL 61, CRL 9096, CRL 1793 and CRL 9618); mouse sertoli cells (TM4, Mather, Biol. Reprod. 23:243 251 (1980)); monkey kidney cells (CV1 ATCC CCL 70); African green monkey kidney cells (VERO-76, ATCC CRL 1587); human cervical carcinoma cells (HeLa, ATCC CCL 2); buffalo rat liver cells (BRL 3A, ATCC CRL 1442); human lung cells (W138, ATCC CCL 75); human liver cells (Hep G2, HB 8065); mouse melanoma cells (NSO); mouse mammary tumor (MMT 060562, ATCC CCL51), TR1 cells (Mather, et al., Annals N.Y. Acad. Sci. 383:44 46 (1982)); canine kidney cells (MDCK) (ATCC CCL 34 and CRL 6253), HEK 293 (ATCC CRL 1573), WI-38 cells (ATCC CCL 75) (ATCC: American Type Culture Collection, Rockville, Md.), MCF-7 cells, MDA-MB-438 cells, U87 cells, A127 cells, HL60 cells, A549 cells, SP10 cells, DOX cells, SHSY5Y cells, Jurkat cells, BCP-1 cells, GH3 cells, 9L cells, MC3T3 cells, C3H-10T1/2 cells, NIH-3T3 cells and C6/36 cells. The use of mammalian tissue cell culture to express polypeptides is discussed generally in Winnacker, FROM GENES TO CLONES (VCH Publishers, N.Y., N.Y., 1987).

Exemplary plant cells include, for example, *Arabidopsis thaliana*, rape seed, corn, wheat, rice, tobacco etc.) (Staub, et al. 2000 Nature Biotechnology 1(3): 333-338 and McGarvey, P. B., et al. 1995 Bio-Technology 13(13): 1484-1487; Bardor, M., et al. 1999 Trends in Plant Science 4(9): 376-380). Exemplary insect cells (for example, *Spodoptera frugiperda* Sf9, Sf21, *Trichoplusia ni*, etc. Exemplary bacteria cells include *Escherichia coli*. Various yeasts and fungi such as *Pichia pastoris, Pichia methanolica, Hansenula polymorpha*, and *Saccharomyces cerevisiae* can also be selected.

Other suitable host cells are known to those skilled in the art.

Methods to make and use host cells of the invention, and to make therapeutic glycoproteins in such host cells are known in the art. For example, methods are provided in *Current Protocols in Cell Biology* (2007, John Wiley and Sons, Inc., Print ISSN: 1934-2500); *Current Protocols in Protein Science* (2007, John Wiley and Sons, Inc., Print ISSN: 1934-3655); Wurm, *Production of recombinant protein therapeutics in cultivated mammalian cells* (2004) Nature Biotech. 22:1393-1398; *Therapeutic Proteins: Methods and Protocols*, Smales and James, eds. (2005, Humana Press, ISBN-10: 1588293904).

Methods to Detect Gene Expression or Activity

Nucleic acid based-detection methods encompass hybridization or amplification assays that include, but are not limited to, Southern or Northern analyses, polymerase chain reaction analyses (e.g., quantitative PCR), SAGE analyses, probe arrays or oligonucleotide arrays. Probes useful in such methods are routinely selected from known gene sequences. In some cases, cellular material from one species, (e.g., one rodent species such as Chinese Hamster) may be evaluated using probes identified from ortholog gene sequences (e.g., rat or mice-derived sequences) found in the art.

Antibody-based techniques for detection of proteins include enzyme linked immunosorbent assays (ELISAs), immunoprecipitations, immunofluorescence, enzyme immunoassay (EIA), radioimmunoassay (RIA), Western blot analysis, surface plasmon resonance. Other methods may include the detection of peptides or fragments thereof using mass spectrometric-based methods, including, but not limited to LC-MS, MS/MS, MS/MS/MS, MALDI-MS, multiple reaction monitoring (MRM).

In one embodiment, detection methods described herein are part of determining a gene expression profile of the sample, wherein the profile includes a value representing the level of a gene's expression, among at least one other value for expression of at least one other gene. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to evaluate or screen CHO cells.

In another aspect, the invention features a computer medium having a plurality of digitally encoded data records. Each data record includes a value representing the level of expression of a gene in a sample, and a descriptor of the sample. The descriptor of the sample can be an identifier of the sample, e.g., the cell type from which the sample was derived (e.g., a CHO cell strain), or a cell culture condition under which the cell that is the source of the sample was cultured. In one embodiment, the data record further includes values representing the level of expression of genes other than Ggta1 (e.g., other genes associated with glycan synthesis, or other genes on an array). The data record can be structured as a table, e.g., a table that is part of a database such as a relational database (e.g., a SQL database of the Oracle or Sybase database environments).

Methods of Modulating Gene Expression

In certain methods of the invention, gene expression is modulated, e.g., increased or reduced. Such methods may include reducing (knocking-down) expression or abolishing (knocking out) expression of a subject gene. Methods of making and using antisense molecules to modulate biological activities are known in the art, see for example: Pan and Clawson, *Antisense applications for biological control* (2006) J. Cell Biochem. 98(1):14-35; Sioud and Iversen, *Ribozymes, DNAzymes and small interfering RNAs as therapeutics* (2005) Curr Drug Targets 6(6):647-53; Bhindi et al., *Brothers in arms: DNA enzymes, short interfering RNA, and the emerging wave of small-molecule nucleic acid-based gene-silencing strategies* (2007) Am J. Pathol. 171(4):1079-88. Methods of making gene knockouts are known in the art, e.g., see Kuhn and Wurst (Eds.) *Gene Knockout Protocols (Methods in Molecular Biology)* Humana Pres (Mar. 27, 2009).

In some embodiments, a cell can be selected which has been genetically engineered for permanent or regulated inactivation of a gene encoding a protein involved with the synthesis of a particular glycan as described herein. For example, genes encoding an enzyme such as the enzymes described herein can be inactivated. Permanent or regulated inactivation of gene expression can be achieved by targeting to a gene locus with a transfected plasmid DNA construct or a synthetic oligonucleotide. The plasmid construct or oligonucleotide can be designed to several forms. These include the following: 1) insertion of selectable marker genes or other sequences within an exon of the gene being inactivated; 2) insertion of exogenous sequences in regulatory regions of non-coding sequence; 3) deletion or replacement of regulatory and/or coding sequences; and, 4) alteration of a protein coding sequence by site specific mutagenesis.

In the case of insertion of a selectable marker gene into coding sequence, it is possible to create an in-frame fusion of an endogenous exon of the gene with the exon engineered to contain, for example, a selectable marker gene. In this way following successful targeting, the endogenous gene expresses a fusion mRNA (nucleic acid sequence plus selectable marker sequence). Moreover, the fusion mRNA would be unable to produce a functional translation product.

In the case of insertion of DNA sequences into regulatory regions, the transcription of a gene can be silenced by disrupting the endogenous promoter region or any other regions in the 5' untranslated region (5' UTR) that is needed for transcription. Such regions include, for example, translational control regions and splice donors of introns. Secondly, a new regulatory sequence can be inserted upstream of the gene that would render the gene subject to the control of extracellular factors. It would thus be possible to down-regulate or extinguish gene expression as desired for glycoprotein production. Moreover, a sequence which includes a selectable marker and a promoter can be used to disrupt expression of the endogenous sequence. Finally, all or part of the endogenous gene could be deleted by appropriate design of targeting substrates.

Other methods of affecting gene expression, e.g., increasing or reducing gene expression, may involve addition of agents, e.g., addition of specified agents to culture media, e.g., as described herein.

Biology of High Mannose Structures

The presence of mannose containing glycans on proteins is known to have an effect on the interaction of these proteins with several receptors and binding partners through which the function, distribution, and stability of these mannose-containing proteins are influenced. Such binding partners includes Fc receptors, FcRn, mannose binding lectins (MBL), C1q, mannose receptor, DC and L-sign, and receptors on specific cells (see, e.g., Li et al., (2009) Curr Opin Biotechnol. 20, 678-684). Thus, methods described herein are useful to evaluate or modulate targeting of glycoproteins to specific tissues (e.g., bone marrow, mammary epithelia, intestinal epithelia), to specific cell types (e.g., dendritic cells, macrophages) or specific compartments (e.g., lysosome). The methods described herein are also useful to evaluate or modulate biological activity through receptor binding (e.g., Fc receptors), serum half lives/clearance (e.g., through binding to the mannose receptor, FcRn) and adsorption.

The methods described herein are also useful to evaluate or modulate other biological activities, including: antibody deposition and aggregation. The glycan structure on the Fc portion of an antibody change the 3 dimensional structure of the antibody. Alterations in antibody structure are known to have the potential to lead to antibody aggregation and deposition. The methods used herein would be useful to generate antibodies with targeted levels of high mannose so as to decrease antibody sera deposition, complex formation and aggregation. Similarly, these structural changes can be utilized to increase or decrease immunogenicity of an antibody.

In some embodiments, the antibody molecules may also contain glycosylation on the Fab portion of the molecule. In these instances, in addition to those biology described above, the presence of a high mannose structure may also alter the affinity for the epitopes, or the ability for the antibody to form cross linked complexes on the cell surface. The methods described herein would be useful to generate antibodies with altered levels of high mannose structures so as to "dial" in desired affinity, as well as achieve a desired level of receptor cross linking so as to decrease off target effects and increase the therapeutic window. In addition design of high mannose containing peptides and polypeptides may inhibit protein degradation through ubiquitin ligase mediated pathway.

Other features and advantages of the invention will be apparent from the following detailed description, and from the claims.

This invention is further illustrated by the following examples that should not be construed as limiting. The contents of all references, patents and published patent applications cited throughout this application are incorporated herein by reference.

EXAMPLES

Example 1: High Throughput Analysis of High Mannose Protein Glycoforms

One of the major challenges in characterizing low abundance glycoforms in a mixture is the presence of higher abundance glycoforms as well as the diverse array of glycoforms in the mixture. The analysis of low abundance glycoforms typically involves the release of the glycans from the protein either by enzymatic (PNGAse-F or Endo-H) or chemical treatment (i.e. hydrazinolysis). The released glycans are then purified and subsequently analyzed without further derivatization or after the labeling with different chromophores/fluorophores. However, the laborious sample preparation steps involved in this process as well as the high amounts of material needed for these analyses hampers the ability to use these types of methods in a high throughput setting.

The method described here is useful to analyze high mannose containing glycoforms, and in particular high mannose glycoforms present in low abundance (e.g., <10%, <5%, <4%, <3%, <2%, <1%, <0.05%).

Starting with a glycoprotein-containing sample such as an antibody sample (e.g., from either media, or a protein preparation) optionally perform a buffer exchange to buffer compatible with enzymatic digest of step #2 and/or mass spectrometry analysis of step #3. This step is optional depending on the sample formulation or the chromatographic method of step 3. Treat the glycoprotein sample with an enzyme that cleaves complex fucosylated glycans from the glycoprotein in the sample (e.g., Endoglycosydase F3 (http://glycotools.qa-bio.com/s.nl/it.A/id.96/.f)). This step unexpectedly reveals low abundance glycoforms such as high mannose species, in the remaining sample. In the next step, optionally reduce and alkylate the sample and/or perform a buffer exchange to buffer compatible with MS. In a next step, analyze the enzymatically treated sample by a reverse phase LC-MS or targeted reverse phase-LC-MS analysis to identify high mannose-containing glycoforms. Other types of column chemistries can also be employed. Knowing the theoretical masses of the high mannose-containing glycoforms, a targeted MS experiment can be established to only monitor selected set of m/z signatures corresponding to these species. The analysis can be repeated with multiple samples in a comparative analysis setting.

The method described above provides an excellent balance between throughput, resolution and sensitivity making it particularly suitable for the analysis of low abundance glycoforms containing high mannose in a high throughput setting.

Example 2: Effect of MGAT1 Levels on Man5 Structures

Figure 2:
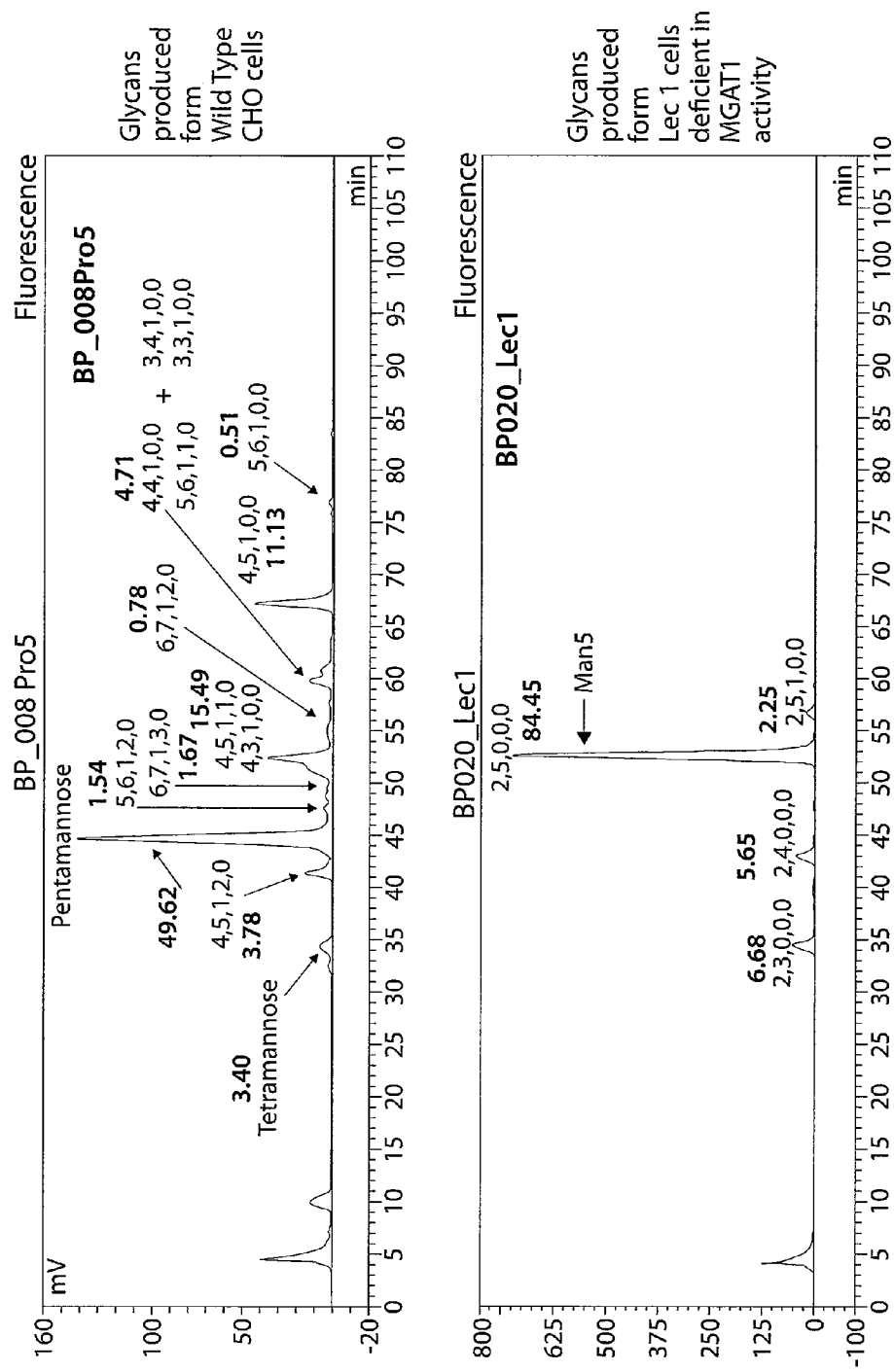
FIG. 2 is a set of LC profiles of glycans harvested from a wild-type cell line (CHO) and a Lec1 mutant (MGAT1 null) cell line.

Wild type CHO (WT) and Lec1 (MGAT1 null) cell lines were stably transformed to express an IgG model fusion protein. The recombinant product was harvested from the cells, and N-glycans analyzed by Amide LC/MS. LC data from WT (top) and MGAT1 deficient (bottom) CHO cells with representative glycans identified with relative percentage is shown in FIG. 2. As can be seen in FIG. 2, the glycoprotein produced from the Lec1 mutant lacks Man5 structures.

Figure 3:
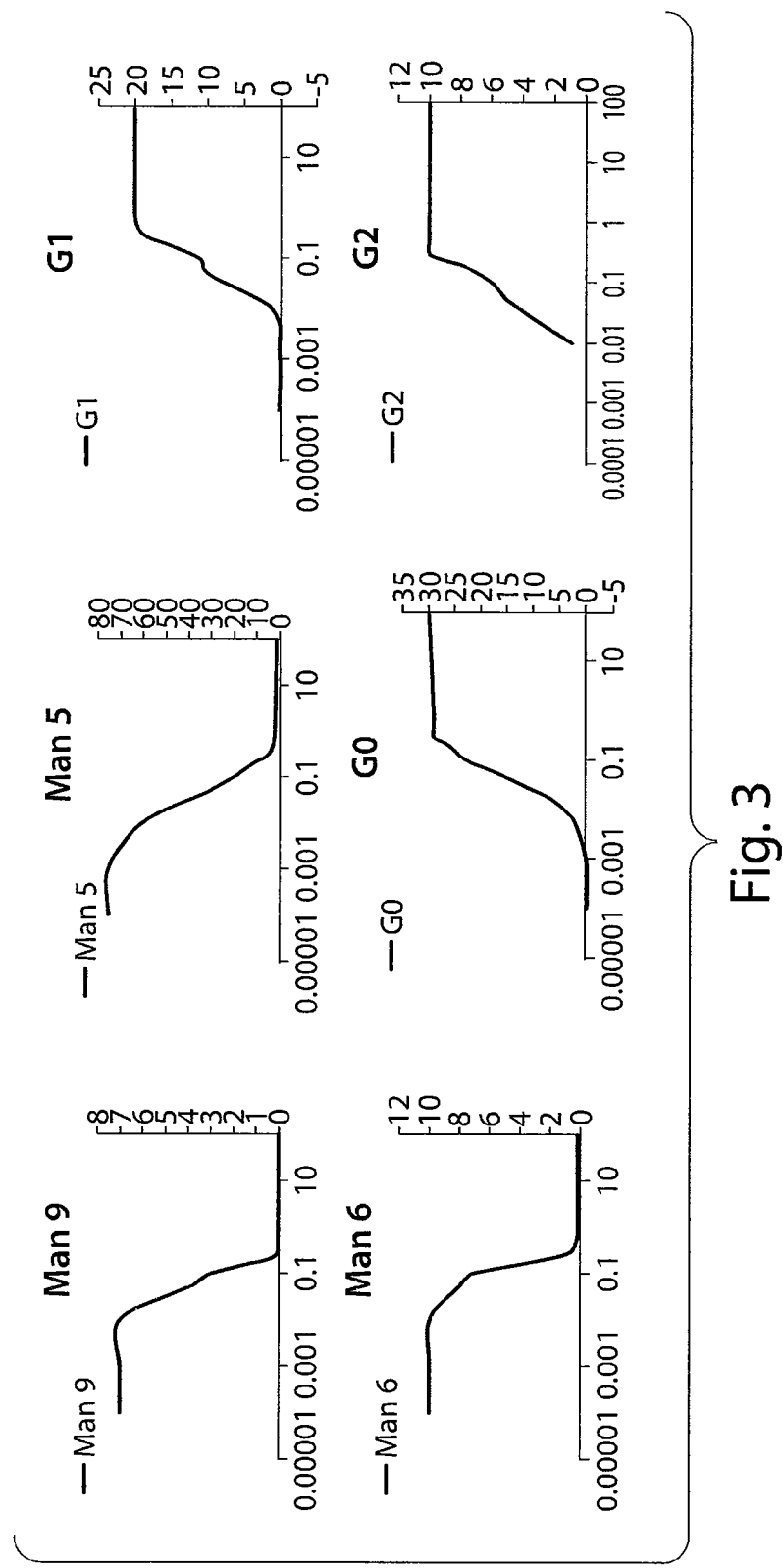
FIG. 3 is a set of plots reflecting glycan levels modeled to reflect varying levels of MGAT1. Each plot refers to the level of the indicated glycan (% of starting) based on the level of MGAT1 expression (% of starting). These illustrate that an elevation of High mannose structures does not require complete abolition of the MGAT1 transferase

However, it has been found that complete inhibition of MGAT1 is not necessary to produce this effect. FIG. 3 a set of plots reflecting glycan levels modeled to reflect varying levels of MGAT1. Each plot refers to the level of the indicated glycan (% of starting) based on the level of MGAT1 expression (% of starting). These illustrate that an elevation of high mannose structures does not require complete abolition ore depletion of the MGAT1 transferase.

Example 3: Identification of Non-Linear Correlations Related to High Mannose Content This example illustrates the identification of unexpected, non-linear correlations between glycosylation regulators and high mannose content.

Figure 4A:
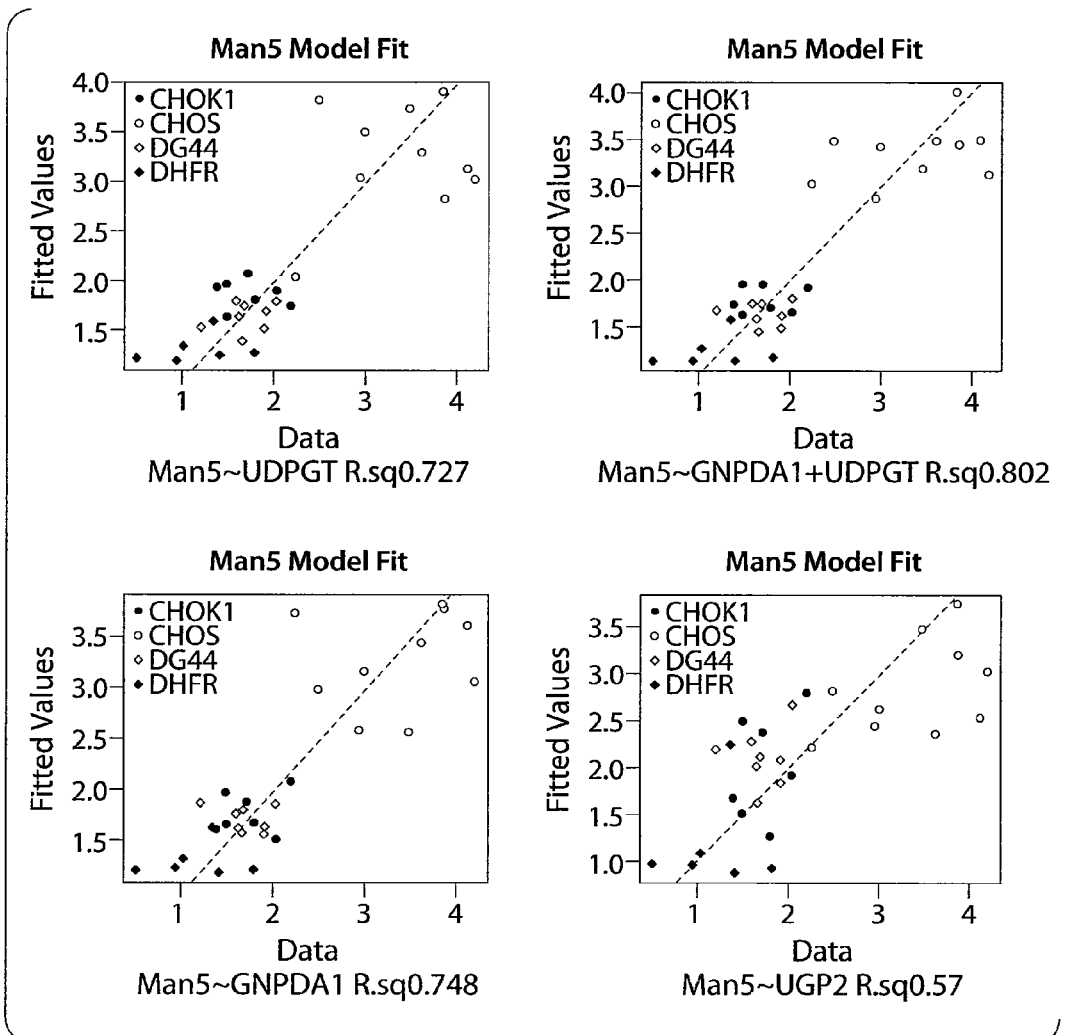
FIG. 4 is a set of plots representing a linear analysis of the expression of the gene UGP-2 in a cell population as it correlates to Man5 content on a glycoprotein produced by the cell. Each dot on this plot indicates a particular clone of one of four listed transformed cell lines.
Figure 4B:
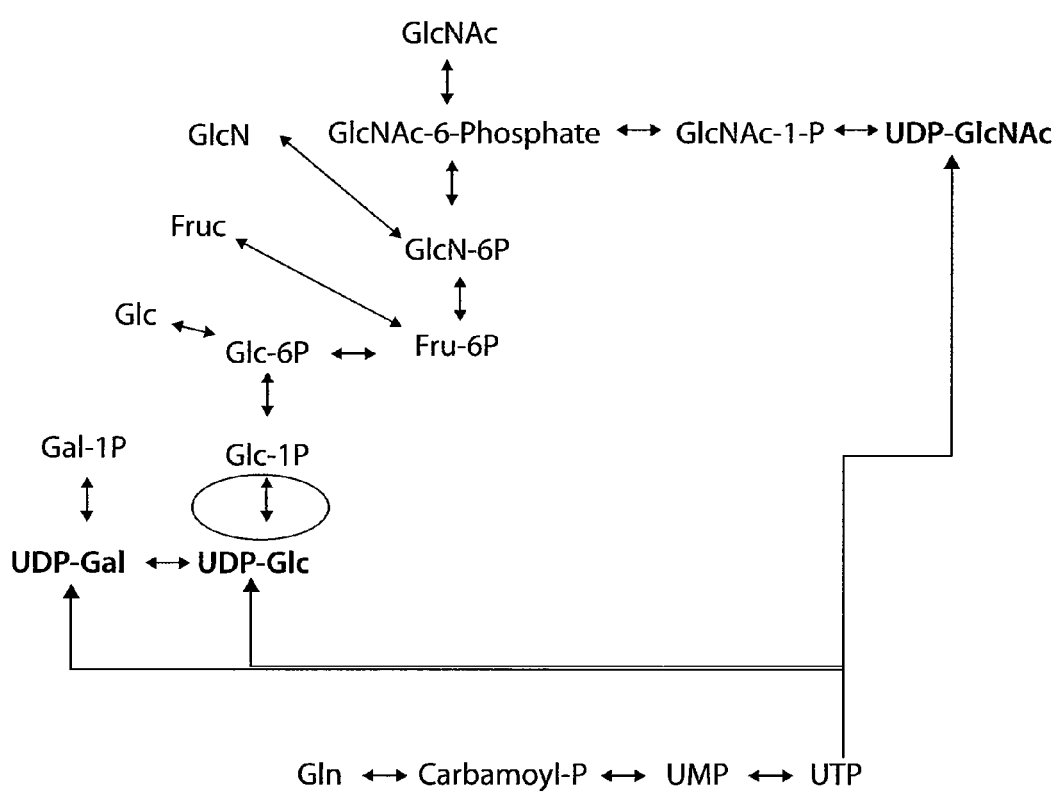

Stably transformed clones expressing an IgG fusion model protein were generated from each of the cell lines CHOK1, CHOS, DG44 and Dhfr-. The IgG product was isolated from each clone and the glycans characterized by 2D LC/MS. The level of Man5 was determined as a percentage of total glycans. Concurrently, mRNA was extracted from each clone and the levels of various enzymes involved in disparate aspects of glycobuilding were characterized. Such enzymes include glycosyltransferases, transporters, metabolic enzymes, and others involved in the biosynthesis of glycans. These data were subjected to linear analysis to identify relations between particular biosynthetic steps and Man5 content. FIG. 4A shows the level of gene expression of UGP-2 as it unexpectedly shows a linear correlation to Man5 content on a glycoprotein produced by the cell. While not bound by theory, FIG. 4B illustrates how this gene can, in retrospect, be correlated to metabolites involved in Man5 biosynthesis.

Example 4: Man5 Levels Affected by High Concentrations of Divalent Cations

This example illustrates the inhibitory affect of elevated levels of divalent cations on glycoenzyme activity.

Figure 5:
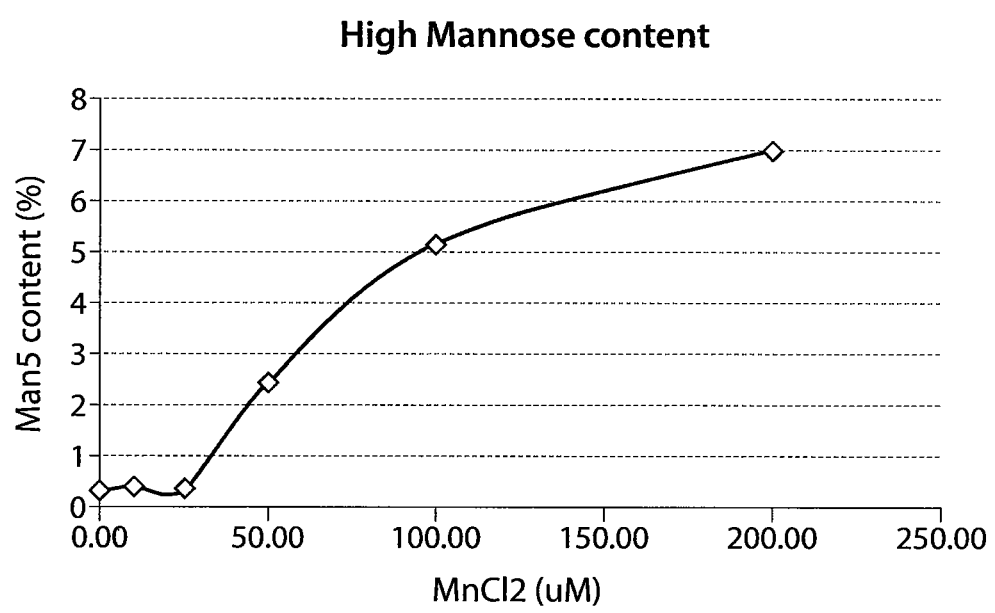
FIG. 5 is a plot of increasing levels of MnC12 vs levels (% of total glyans) of Man5. The data represent duplicate determinants.

CHO cells expressing an IgG fusion model protein were cultured in the presence of increasing levels of $MnCl_2$. Product was harvested from these cells after 5 days, purified, and subjected to N-glycan analysis by normal phase HPLC. The levels (% of total glyans) of Man5 were quantified and are shown in FIG. 5. As can be seen, as the levels of Mn in the media are elevated there is a concommittant increase in high mannose content. While not bound by theory, this may be driven primarily by Mn cofactor activity on transferases.

Extensions and Alternatives

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way. While the methods have been described in conjunction with various embodiments and examples, it is not intended that the methods be limited to such embodiments or examples. On the contrary, the methods encompass various alternatives, modifications, and equivalents, as will be appreciated by those of skill in the art.

We claim:

1. A method of quantifying high mannose glycans on a therapeutic glycoprotein, the method comprising:
   (a) providing a sample of a therapeutic glycoprotein, wherein said therapeutic glycoprotein comprises glycoforms containing high mannose glycans, wherein said high mannose glycans are present in an abundance of less than 20% relative to the total glycan mass of the glycoprotein in said sample,
   (b) treating said sample of said therapeutic glycoprotein with Endoglycosidase F3, to produce a processed therapeutic glycoprotein comprising at least one high mannose glycan; and
   (c) quantifying said at least one high mannose glycan remaining on said processed therapeutic glycoprotein after step (b), wherein said at least one high mannose glycan is present in an abundance of less than 20% relative to the total glycan mass of the glycoprotein sample.

2. The method of claim 1, wherein said quantifying step (c) comprises performing capillary electrophoresis (CE), reverse phase LC-MS or targeted reverse phase-LC-MS on the said processed therapeutic glycoprotein.

3. The method of claim 1, further comprising determining one or more of:
   (i) the amount of high mannose glycans on said processed therapeutic glycoprotein relative to the total glycans on said therapeutic glycoprotein;
   (ii) one or more relative ratios of two high mannose species selected from Man4, Man5, Man6, Man7, Man8, and Man8, remaining on said processed therapeutic glycoprotein;
   (iii) the relative ratio of high mannose glycans remaining on said processed therapeutic glycoprotein to hybrid structures on said therapeutic glycoprotein,
   (iv) the relative ratio of high mannose glycans remaining on said processed therapeutic glycoprotein to complex structures remaining on said glycoprotein,
   (v) the relative ratio of high mannose glycans remaining on said processed therapeutic glycoprotein to fucosylated structures remaining on said processed therapeutic glycoprotein;
   (vi) the presence or abundance of modified high mannose glycans remaining on said processed therapeutic glycoprotein.

4. The method of claim 1, wherein said method further comprises separately quantifying at least two individual glycans remaining on said processed therapeutic glycoprotein.

5. The method of claim 1, wherein said therapeutic glycoprotein is an antibody or a receptor-Fc fusion.

6. The method of claim 5, wherein said antibody is a pharmaceutical preparation produced from a mammalian cell culture.

7. The method of claim 1, wherein said method is performed under good manufacturing practice (GMP) conditions.

8. The method of claim 1, further comprising comparing the quantified amount of high mannose glycans remaining on the processed therapeutic glycoprotein to a reference level or a quality criterion.

9. The method of claim 3, wherein said modified high mannose glycans remaining on said processed therapeutic glycoprotein are fucosylated high mannose glycans.

10. The method of claim 1, further comprising performing a buffer exchange to a buffer compatible with enzymatic digest and/or mass spectrometry (MS) analysis.

11. The method of claim 1, further comprising reducing and alkylating said processed therapeutic glycoprotein and/or performing a buffer exchange to a buffer compatible with mass spectrometry.

12. The method of claim 8, wherein said reference level is that of a control sample, a GMP standard, or a pharmaceutical standard.

* * * * *